US007384654B2

(12) United States Patent
Menon et al.

(10) Patent No.: US 7,384,654 B2
(45) Date of Patent: Jun. 10, 2008

(54) ANTI-ALLERGY COMPOSITION AND RELATED METHOD

(75) Inventors: Gopl R. Menon, Riverside, CA (US); David J. Fast, Grand Rapids, MI (US); David W. Krempin, Temecula, CA (US); John N. Goolsby, Hudsonville, MI (US)

(73) Assignee: Access Business Group International LLC, Ada, MI (US)

( * ) Notice: Subject to any disclaimer, the term of this patent is extended or adjusted under 35 U.S.C. 154(b) by 307 days.

(21) Appl. No.: 11/051,905

(22) Filed: Feb. 4, 2005

(65) Prior Publication Data

US 2005/0175718 A1 Aug. 11, 2005

Related U.S. Application Data

(60) Provisional application No. 60/542,070, filed on Feb. 5, 2004.

(51) Int. Cl.
*A61K 36/00* (2006.01)
*A61K 31/19* (2006.01)

(52) U.S. Cl. .................. 424/725; 424/739; 424/756; 514/569

(58) Field of Classification Search ............... 424/725, 424/739, 756; 514/25
See application file for complete search history.

(56) References Cited

U.S. PATENT DOCUMENTS

| 5,618,543 | A | 4/1997 | Harris et al. |
| 5,747,006 | A * | 5/1998 | Dornoff et al. ............... 424/62 |
| 6,027,716 | A * | 2/2000 | Levin et al. .................. 424/58 |
| 6,180,106 | B1 | 1/2001 | Keller et al. |
| 6,193,995 | B1 | 2/2001 | Zhenzhen et al. |
| 6,210,680 | B1 | 4/2001 | Jia et al. |
| 6,217,875 | B1 | 4/2001 | Murai et al. |
| 6,251,383 | B1 | 6/2001 | Upadhyay et al. |
| 6,290,993 | B1 | 9/2001 | Anderson et al. |
| 6,383,525 | B1 | 5/2002 | Hsu et al. |
| 6,432,455 | B2 | 8/2002 | Keller et al. |
| 6,451,354 | B1 | 9/2002 | Hebert et al. |
| 6,503,542 | B2 | 1/2003 | Sheu |
| 6,524,627 | B1 | 2/2003 | Kim et al. |
| 6,538,021 | B1 * | 3/2003 | Buchholz et al. ............ 514/456 |
| 6,551,626 | B1 | 4/2003 | Koch et al. |
| 6,630,176 | B2 | 10/2003 | Li et al. |
| 6,641,846 | B2 | 11/2003 | Zhang et al. |
| 6,759,061 | B2 * | 7/2004 | Watson et al. ............... 424/725 |
| 2001/0000144 | A1 | 4/2001 | Keller et al. |
| 2001/0024664 | A1 | 9/2001 | Obukowicz et al. |
| 2002/0022060 | A1 | 2/2002 | Mathur et al. |
| 2002/0031559 | A1 | 3/2002 | Liang et al. |
| 2002/0048594 | A1 | 4/2002 | Breton et al. |
| 2002/0090402 | A1 | 7/2002 | Zhang et al. |
| 2002/0098269 | A1 | 7/2002 | Bank et al. |
| 2002/0106415 | A1 | 8/2002 | Iwase et al. |
| 2002/0122833 | A1 | 9/2002 | Sheu |
| 2002/0142055 | A1 | 10/2002 | De Souza et al. |
| 2003/0017217 | A1 | 1/2003 | Almagro et al. |
| 2003/0050278 | A1 | 3/2003 | Onishi et al. |
| 2003/0082245 | A1 | 5/2003 | Tani |
| 2003/0082246 | A1 | 5/2003 | Tani |
| 2003/0096020 | A1 | 5/2003 | Brindavanam et al. |
| 2003/0129265 | A1 | 7/2003 | Iwase et al. |
| 2003/0157126 | A1 | 8/2003 | Li et al. |
| 2003/0170331 | A1 | 9/2003 | Cals-Grierson et al. |
| 2003/0185911 | A1 | 10/2003 | Qazi et al. |
| 2003/0190378 | A1 | 10/2003 | Kim et al. |
| 2003/0198697 | A1 | 10/2003 | Yoshida |
| 2003/0224067 | A1 | 12/2003 | Wen |
| 2003/0228379 | A1 | 12/2003 | Shi et al. |
| 2003/0228383 | A1 | 12/2003 | Doshi et al. |
| 2004/0018251 | A1 | 1/2004 | Koch et al. |
| 2004/0028643 | A1 | 2/2004 | Chiba et al. |
| 2004/0043084 | A1 | 3/2004 | Cloca et al. |
| 2004/0047832 | A1 | 3/2004 | Pauly et al. |
| 2004/0052870 | A1 | 3/2004 | Obukowicz et al. |
| 2004/0052880 | A1 | 3/2004 | Kobayashi et al. |
| 2004/0071796 | A1 | 4/2004 | Li |
| 2004/0076692 | A1 | 4/2004 | Van Norren et al. |
| 2004/0081710 | A1 | 4/2004 | Feng |
| 2004/0131709 | A1 | 7/2004 | Berdahl et al. |
| 2004/0185122 | A1 | 9/2004 | Obukowicz et al. |

FOREIGN PATENT DOCUMENTS

CN 1073865 7/1993

(Continued)

OTHER PUBLICATIONS

Majima T, et al.; Pharmaceutical evaluation of liquorice before and after roasting in mice; J Pharm Pharmacol. May;56(5); 2004:589-95.

(Continued)

*Primary Examiner*—Christopher R Tate
*Assistant Examiner*—Randall Winston
(74) *Attorney, Agent, or Firm*—Warner Norcross & Judd LLP

(57) ABSTRACT

An composition and related method that prevents, inhibits and/or mitigates an allergic response by down regulating the production of IgE, down regulating the binding of IgE antibodies to receptors on cells, and/or inhibiting allergy mediators, for example, histamine, prostoglandin $D_2$, or luekotriene $C_4$ release. The composition comprises at least one of the following ingredients: luteolin from Perilla leaf or seed, Cinnamon, Kiwi, Picao preto, Hesperidin, Acerola cherry, Guaco, Holy Basil, Kakadu, Solamum, Rosmarinic acid, Tinospora and Aframomum. In one embodiment, the composition at least three different ingredients selected from Cinnamon, Acerola, Luteolin and Picao preto. Optionally, these ingredients can be combined with at least one of Aframomum, Rosmarinic acid, and Tinospora. The composition is administered with effective amounts to prevent, inhibit and/or mitigate allergic responses.

8 Claims, 14 Drawing Sheets

FOREIGN PATENT DOCUMENTS

| | | |
|---|---|---|
| CN | 1076089 | 9/1993 |
| CN | 1078118 | 11/1993 |
| CN | 1078620 | 11/1993 |
| CN | 1082335 | 2/1994 |
| CN | 1104872 | 7/1995 |
| CN | 1110532 | 10/1995 |
| CN | 1112431 | 11/1995 |
| CN | 1113717 | 12/1995 |
| CN | 1121783 | 5/1996 |
| CN | 1127645 | 7/1996 |
| CN | 1138468 | 12/1996 |
| CN | 1145733 | 3/1997 |
| CN | 1152420 | 6/1997 |
| CN | 1153778 | 7/1997 |
| CN | 1266693 | 9/2000 |
| CN | 1277872 | 12/2000 |
| CN | 1299656 | 6/2001 |
| CN | 1310007 | 8/2001 |
| CN | 1319420 | 10/2001 |
| CN | 1366834 | 9/2002 |
| CN | 1370589 | 9/2002 |
| DE | 2002-098648 | * 11/2001 |
| EP | 1205475 | 5/2002 |
| JP | 61-263924 | 11/1986 |
| JP | 63-036744 | 2/1988 |
| JP | 01-102027 | 4/1989 |
| JP | 01-121217 | 5/1989 |
| JP | 02-227030 | 10/1990 |
| JP | 02-290812 | 11/1990 |
| JP | 04-063579 | 2/1992 |
| JP | 04-079852 | 3/1992 |
| JP | 04-290822 | 10/1992 |
| JP | 04-297418 | 10/1992 |
| JP | 04-342523 | 11/1992 |
| JP | 05-003753 | 1/1993 |
| JP | 05-058902 | 3/1993 |
| JP | 05-178255 | 7/1993 |
| JP | 05-227891 | 9/1993 |
| JP | 06-062795 | 3/1994 |
| JP | 06-070717 | 3/1994 |
| JP | 06-293652 | 10/1994 |
| JP | 07-017859 | 1/1995 |
| JP | 07-252161 | 3/1995 |
| JP | 07-215884 | 8/1995 |
| JP | 08-073314 | 3/1996 |
| JP | 08-116891 | 5/1996 |
| JP | 08-119875 | 5/1996 |
| JP | 08-333267 | 12/1996 |
| JP | 09-020672 | 1/1997 |
| JP | 09-087189 | 3/1997 |
| JP | 09-121766 | 5/1997 |
| JP | 09-291299 | 11/1997 |
| JP | 10-000070 | 1/1998 |
| JP | 10-028549 | 2/1998 |
| JP | 10-072338 | 3/1998 |
| JP | 10-099046 | 4/1998 |
| JP | 10-139679 | 5/1998 |
| JP | 10-298098 | 11/1998 |
| JP | 11-056297 | 3/1999 |
| JP | 11-056927 | 3/1999 |
| JP | 2000-053550 | 2/2000 |
| JP | 2000-086510 | 3/2000 |
| JP | 2001-064192 | 3/2001 |
| JP | 2001-354579 | 12/2001 |
| JP | 2002-154979 | 5/2002 |
| JP | 2002-526384 | 8/2002 |
| JP | 2002-360184 | 12/2002 |
| JP | 2003-002811 | 1/2003 |
| JP | 2003-128558 | 5/2003 |
| JP | 2003-169631 | 6/2003 |
| JP | 2001-592583 | * 7/2003 |
| JP | 2003-201246 | 7/2003 |
| JP | 2003-252786 | 9/2003 |
| JP | 2003-321386 | 11/2003 |
| JP | 2004-010488 | 1/2004 |
| JP | 2004-018492 | 1/2004 |
| KR | 000015793 A | 3/2000 |
| KR | 000024484 A | 5/2000 |
| KR | 100279902 B1 | 11/2000 |
| KR | 000072988 A | 12/2000 |
| KR | 010025574 A | 4/2001 |
| KR | 010074415 A | 8/2001 |
| KR | 010076109 A | 8/2001 |
| KR | 010076110 A | 8/2001 |
| KR | 010076111 A | 8/2001 |
| KR | 010076112 A | 8/2001 |
| KR | 010076113 A | 8/2001 |
| KR | 010084813 A | 9/2001 |
| KR | 1020020006643 A | 1/2002 |
| KR | 1020020013134 A | 2/2002 |
| KR | 1020020089275 A | 11/2002 |
| KR | 1020030056582 A | 7/2003 |
| WO | WO 2001-066122 | 9/2001 |
| WO | WO 2002-009699 | 2/2002 |
| WO | WO 2002-062365 | 8/2002 |
| WO | WO 2004-037180 | 5/2004 |
| WO | WO 2004/056382 | 7/2004 |

OTHER PUBLICATIONS

Motohashi N, et al.; Biological activity of barbados cherry (acerola fruits, fruit of Malpighia emarginata DC) extracts and fractions; Phytother Res. Mar;18(3); 2004:212-23.

Takano H, et al.; Extract of Perilla Frutescens enriched for rosmarinic acid, a polyphenolic phytochemical, inhibits seasonal allergic rhinoconjunctivitis in humans; Exp Biol Med (Maywood). Mar;229(3); 2004:247-54.

Park EK, et al.; Ginsenoside RH1 possesses antiallergic and anti-inflammatory activities; Int Arch Allergy Immunol. Feb;133(2); 2004:113-20; Epub Jan. 21, 2004.

Dimo T, et al.; Possible mechanisms of action of the neutral extract from *Bidens pilosa* L. leaves on the cardiovascular system of anaesthetized rats; Phytother Res. Dec;17(10); 2003:1135-9.

Yamamoto Y, et al.; Pharmaceutical evaluation fo *Glycyrrhiza uralensis* roots cultivated in eastern Nei-Meng-Gu of China; Biol Pharm Bull. Aug;26(8); 2003:1144-9.

Haggag EG, et al.; The Effect of a Herbal Water-Extract on Histamine Release from Mast Cells and on Allergic Asthma; J Herb Pharmcother. 3(4); 2003:41-54.

Raulf-Heimsoth M, et al.; Anaphylactic reaction to apply juice containing acerola: cross-reactivity to latex due to prohevein; J Allergy Clin Immunol. Apr; 109(4); 2002:715-6.

Gonzalez P, et al.; Immunotherapy with an extract of *Olea europaea* quantified in mass units. Evaluation of the safety and efficacy after one year of treatment; J Investig Allergol Clin Immunol.12(4); 2002:263-71.

Lee YM, et al.; Inhibition of immunologic and nonimmunologic stimulation-mediated anaphylactic reactions by water extract of white eggplant (*Solanum melongena*). Pharmacol Res. Apr;43(4); 2001:405-9.

Jeong HJ, et al.; Inhibitory effects of mast cell-mediated allergic reactions by cell cultured Siberian Ginseng; Immunopharmacol Immunotoxicol. Feb;23(1); 2001:107-17.

Shin TY, et al.; Inhibitory effect of mast cell-mediated immediate-type allergic reactions in rats by *Perilla frutescens*; Immunopharmacol Immunotoxicol Aug;22(3); 2000:489-500.

Pereira RL, et al.; Immunosuppressive and anti-inflammatory effects of methanolic extract and the polyacetylene isolated from *Bidens pilosa* L.; Immunopharmacology. Jun;43;(1); 1999:31-7.

Ishihara T, et al.; Inhibition of antigen-specific T helper type 2 responses by *Perilla frutescens* extract [Article in Japanese]; Arerugi. Apr;48(4); 1999:443-50.

Watanabe S, et al.; A high alpha-linolenate diet suppresses antigen-induced immunoglobulin E response and anaphylactic shock in mice; J Nutr. Sep;124(9); 1994:1566-73.

Imaoka K, et al.; Effects of *Perilla frutescens* extract on anti-DNP lgE antibody production in mice [Article in Japanese]; Arerugi. Jan;42(1); 1993:74-80.

Macchia L, et al. Changes in skin reactivity, specific lgE and lgG levels after one year of immunotherapy in olive pollinosis; Allergy. Aug;35(5); 1991:410-8.

Geissberger P, et al.; Constituents of *Bidens pilosa* L.: do the components found so far explain the use of this plan in traditional medicine? Acta Trop. Feb;48(4); 1991:251-61.

Subiza J, et al. Allergic conjuctivitis to chamomile tea; Ann Allergy Aug;65(2); 1990:127-32.

Nagai H, et al.; Immunopharmacological studies of the aqueous extract of *Cinnamomum cassia* (CCAq). l. Anti-allergic action.; Jpn J Pharmacolo. Oct;32(5); 1982:813-22.

Koda A, et al. Anti-allergic actions of traditional oriental medicine—actions against types I and IV hypersensitivity reactions [Article in Japanese]; Nippon Yakurigaku Zasshi. Jul;80(1); 1982:31-41.

Ishikura, N.; Anthocyanins and Flavones in Leaves and Seeds of Perilla Plant; Agric. Biol. Chem. 45(8), 1981:1855-1860.

Thatte, UM, et al.; *Tinospora cordifolia* Induces Colony Stimulating Activity in Serum; J Postgrad Med 40(4); 1994:202-3.

Hungerford, NL, et al.; Isolation and Structure of Some Constituents of the Australian Medicinal Plant *Tinospora smilacina* ('Snakevine'); Aust. J. Chem. 51 (1998):1103-1111.

G. Kuttan, SM; Immunomodulatory and antitumour activities of *Tinospora cordifolia*; Fitoterapia 70; (1999):35-43.

Bhattacharya SK, et al. Modulation of humoral immune responses by *Tinospora malabarica* in experimental animals; Indian J Exp Biol Oct;29(10); 1991:971-2. Downloaded from internet; http://www.ncbi.nlm.nih.gov:80/entrez/qu...b=PubMed&list_uids=1726092&dopt+Abstract.

Yukozawa T, et al.; Inhibition of nitric oxide release by an aqueous extract of *Tinospora tuberculata*; Phytother Res Feb;14(1); 2000:51-53.

Downloaded from internet: http://www.ncbi.nlm.nih.gov:80/entrez/qu...b=PubMed&list_uids=10641050&dopt=Abstract.

Guerin M, et al.; *Haematococcus astaxanthin*: applications for human health and nutrition; Trends in Biotechnology, Elsevier Publications May;21(5); 2003:210-216.

Fernandez De La Pradilla, C.; Des plantes qui nous ont gueris; Burkina Faso, 1981 1:208. Downloaded from internet: http://www.metafro.be/prelude/view_symptom?si=H(097).

Makino, T.; Anti-allergic Effect of *Perilla frutescens* and Its Active Constituents; Phytother. Res. 17; (2003):240-243.

Qin, B.; Cinnamon extract (traditional herb) potentiates in vivo insulin-regulated glucose utilization via enhancing insulin signaling in rats; Diabetes Research and Clinical Practice 62; (2003):139-148.

Hirano, T, et al.; Flavonoids such as Luteolin, Fisetin and Apigenin Are Inhibitors on Interleukin-4 and Interleukin-13 Production by Activated Human Basophils; Int Arch Allergy Immunol 2004; 134:135-140.

Konning, GH, et al.; Antimicrobial activity of some medicinal plants from Ghana; Fitoterapia 75; (2004):65-67.

Sanbongi, C, et al.; Rosmarinic Acid inhibits lung injury induced by diesel exhaust particles; Free Radical Biology & Medicine 2003; 34(8):1060-1069.

Badare, VA, et al.; Efficacy of *Tinospora cordifolia* in allergic rhinitis; Journal of Ethnopharmacology 2005; 96:445-449.

Wohlmuth, H.; Perilla Seed Extract; Botanical Pathways_; 10:2-4.

Unknown; RevAyur, Anti-Allergy Herbal Supplement; RevAyur Herbal Supplements, 2003. Advertisement Downloaded from internet: http://www.revayur.com/products/aa.php.

Unknown; *Perillae frutescentis* Labiatae; Hollistic-on-line.com, 2003. Advertisement Downloaded from internet: http://www.holistic-online.com/Herbal-Med/_Herbs/h402.htm.

Unknown; Guaco; Raintree Nutrition, Inc. 2003:1-4, Description Downloaded from internet: http://www.raintree-health.co.uk/plants/guaco.html.

Drexler, HG, et al.; Malignant hematopoietic cell lines: in vitro models for the study of mast cell leukemia; Leuk Res. Aug;27(8); 2003:671-6.

Camargo, EM, et al.; Diuretic effect of the aqueous extract of *Bidens odorata* in the rat; Journal of Ethnopharmacology 95; (2004):363-366.

Andrade-Neto, VF, et al.; Antimalarial Activity of *Bidens pilosa* L. (Asteraceae) Ethanol Extracts From Wild Plants Collected in Various Localities or Plants Cultivated in Humus Soil; Phytother. Res. 18; (2004):634-639.

Khan, MR, et al.; Anti-microbial activity of *Bidens pilosa Bischofia javanica, Elmerillia papuano* and *Sigesbekia orientalis*; Fitoterapia 72; (2001);662-665.

Kay, AB; Allergy and Allergic Diseases; N Engl J Med 34(1); 2001:30-37.

Koning, GH, et al.; Antimicrobial activity of some medicinal plants from Ghana; Fitoterapia 75; (2004):65-67.

Sanbongi, C., et al.; Rosmarinic acid in perilla extract inhibits allergic inflammation induced by Mite allergen, in a mouse model; Clin Exp Allergy 34; (2004):971-977.

Hwang, J., et al.; Soy and Alfalfa Phytoestrogen Extracts Become Potent Low-Density Lipoprotein Antioxidants in the Presence of Acerola Cherry Extract; J. Agric. Food Chem. 49; (2001):308-314.

Mau, J., et al.; Antimicrobial Effect of Extracts from Chinese Chive, Cinnamon, and Corni Fructus; J. Agric. Chem. 49; (2001):183-188.

Tabak, M., et al.; Cinnamon extracts; inhibitory effect on *Helicobacter pylori*; Journal of Ethnopharmacology 67 (1999):269-277.

Pereira, R., et al.; Immunosuppressive and anti-inflammatory effects of methanolic extract and the polyacetylene isolated from *Bidens pilosa* L.; Immunopharmacology 43 (1999):31-37.

Ford, ES, et al.; Serum Antioxidant Concentrations Among U.S. Adults with Self-Reported Asthma; Journal of Asthma 41(2); 2004:179-187.

Harik-Khan, RI, et al.; Serum Vitamin Levels and the Risk of Asthma in Children; American Journal of Epidemiology 159(4); 2004:351-357.

Olusi, SO, et al.; Plasma and white blood cell ascorbic acid concentrations in patients with bronchial asthma; Clinica Chimica Acta 92; (1979):161-166.

Yoshimoto, T., et al.; Flavonoids: Potent Inhibitors of Arachidonate 5-Lipoxygenase; Biochemical and Biophysical Research Communications 116(2); 1983:612-618.

Rege, NN, et al.; Modulation of immunosuppression in obstructive jaundice by *Tinospora cordifolia*, Indian J Med Res 90; (1989):478-483.

Rege, N, et al.; Immunotherapy with *Tinospora cordifolia*: A New Lead in the Management of Obstructive Jaundice; Indian J Gastroenterol 12(1); 1993:5-8.

Dhar, ML, et al.; Screening of Indian Plants for Biological Activity: Part I; Inaian J Exp Biol 6; (1968):232-247.

Meletis, CD; Nutrient Support to Minimize the Allergic Cascade; Alternative & Complementary Therapies (1999):102-105.

Chih, H, et al.; Anti-inflammatory Activity of Taiwan Folk Medicine "Ham-Hong-Chho" in Rats; American Journal of Chinese Medicine XXIII(3-4); 1995:273-278.

Bonina, F., et al.; Evaluation of food supplementation with Anallergy on hystamine and allergen-induced skin reactions in humans; Universita di Catania (Italy) (undated).

Nagai, H., et al.; Immunopharmacological Studies of the Aqueous Extract of *Cinnamomum Cassia* (CCAq); Japan. J. Pharmacol. 32; (1983):813-822.

Unknown; Summary Report; Cadila Pharmaceuticals Ltd. (undated).

Hiroyo, Y.; A Trend in Development of New Food Materials. Antiallergic Effects of Polyphenol Contained in Beefsteak Plant. Orizayuka Shokuhin Kogyo 40(22); 1997:43-48,Fig. 8, Tbl. 1, Ref. 7.

Hiroyo, Y., et al.; Arachidonic acid lipoxygenbase ihibitory components containing in perilla (*Perilla frutescens* var. frutescens) oil cake; Minist. of Agric., For. and Fish., Shikoku Natl. Agric. Exp. Stn. Shokuhin Kenkyu Seika Joho, 9 (1997):18-19, Fig. 4, Ref. 1.

Noriko, K., et al.; Effects of Perilla Extract on Arachidonic Acid Metabolism; Minist. of Agric., For. and Fish., Shikoku Natl. Agric. Exp. Stn. Shikoku Nogyo Shikenjo Hokoku (Bulletin of the Shikoku National Agricultural Experiment Station), 61; (1997):23-29, Fig. 6, Ref. 12.

Oh-Hashi, K., et al.; Possible mechanisms for the differential effects of high linoleate safflower oil and high alpha-linolenate perilla oil diets on platelet-activating factor prpoduction by rat polymorphonuclear leukocytes; Journal of lipid mediators and cell signalling (Netherlands) 17(3); 1997:207-20.

Kohyama, N., et al.; Effects of perilla extract on arachidonic acid metabolism; Bulletin of the Shikoku National Agricultural Experiment Station 0(61); 1997:23-29.

Watanabe, K., et al.; Syosaiko-to and Saiboku-to (Chinese-Japanese herbal medicine) suppress the release of arachidonic acid metabolites from cultured porcine pulmonary artery endothelial cells; Journal of Ethnopharmacology 43(3); 1994:191-196.

Horii, T., et al.; Effect of Dietery Alpha-linolenate on platelet-activating-factor production in rat peritoneal polymorphonuclear leukocytes; Journal of Immunology 147(5); 1991:1607-1613.

Horii, T., et al.; Effect of dietary alpha-linolenate on platelet-activating factor production in rat peritoneal polymorphonuclear lcukocytes; Journal of immunology (Baltimore, Md.—1950) (147(5); 1991:1607-13.

Oh-Hashi, K., et al,; Reevaluation of the effect of a high alpha-linolenate and a high linoleate diet on antigen-induced antibody and anaphylactic responses in mice; Biological and Pharmaceutical Bulleting (Biol. Pharm. Bull.) (Japan) 20(3); 1997:217-223.

Park, JH., et al.; Changes in ether-linked phospholipids in rat-kidney by dietary alpha-linolenic acid in vivo; Lipids 30(6); 1995:541-546.

Koga, T., et al.; Linoleic and alpha -linolenic acids differently modify the effects of elaidic acid on polyunsaturated fatty acid metabolism and some immune indices in rats; British Journal of Nutrition 77(4); 1997:645-656.

Tsugeno, H., et al.; Diet therapy with A-linolenic acid-enriched perilla seed oil on pulmonary emphysema; Okadai Misasa Bun'in Kenkyu Hokoku (Annual Reports of Misasa Medical Branch, Okayama University Medical School) 68; 1997:99-106, Fig. 3, Tbl. 3, Ref. 31.

Nagasawa, H., et al.; Effects of Perilla and Fish Oils on the Acute Stage of Ulcerative Colitis in Rats Induced by Trinitrobenzene Sulfonic Acid; Nippon Eiyo, Shokuryo Gakkaishi (Journal of Japanese Society of Nutrition and Food Science) 50(4); 1997:279-285, Fig. 6, Tbl. 5, Ref. 28.

Ashida, K., et al.; Dietary supplementation with n-3 fatty acids in bronchial asthma correlated with teh generation of LTB4 and LTC4; Okadai Misasa Bun'in Kenkyu Hokoku (Annual Reports of Misasa Medical Branch, Okayama University Medical School) 67; 1996:35-42; Fig. 5, Ref. 26.

Inui, K., et al.; The effect of alpha-linolenic acid-rich emulsion on fatty acid metabolism and leukotriene generation of the colon in a rat model with inflammatory bowel disease; Annals of nutrition and metabolism (Switzerland) 40(3); 1996:175-82.

Gatchalian-Yee, M., et al.; Effect of dietary fats on cholesterol metablism and eicosanoid production in hamsters fed undigested fraction of soybean protein; Journal of Nutritional Science and Vitaminology 40(5); 1994:499-504.

Ito, K., et al.; Effect of the alpha —linolenic acid enriched diet on atophic dermatitis. A pilot study on 6 outpatients. Japanese Journal of Pediatric Allergy and Clinical Immunology 6(3); 1992:87-92.

Unknown; Geni Herbs Brochure for Tinofend. 2001-2003.

Johnston CS, et al, Antihistamine effect of supplemental ascorbic acid and neutrophil chemotaxis, J Am Coll Nutr 1992; 110:662-668.

Ogasawara H, et al, Effect of selected flavonoids on histamine release and hydrogen peroxide generation by human leukocytes, J Allergy Clin Immunol 1984; 75: 184.

Bonina F, et al, In vitro antioxidant and in vivo photo-protective effect of a lyophilized extract of *Capparis spinosa* L. buds, J Cosm Sci 2002; 53:321-335.

Gruenwald J, et al, PDR for Herbal Medicines, 1st ed. Montvale, NJ: Medical Economics Company, Inc., 1998; 65-66, 199-201, 400, 631-632, 689-691.

Trombetta, Domenico et al, Antiallergic and Antihistaminic Effect of Two Extracts of *Capparis spinosa* L. Flowering Buds, Phytother. Res. 19, 29-33 (2005).

Unknown, Geni Herbs Tinofend product information, downloaded from http://www.geniherbs.com/tinofend.html on Sep. 15, 2005.

Lans, C et al, Medicinal and ethnoveterinary remedies of hunters in Trinidad, BMC Compl. & Alern Med 2001; 1:10.

Foreman, JC, Mast cells and the action flavonoids, J Allergy Clin Immunol 1981; 68:546-550.

Reid D, A handbook of Chinese healing herbs, Boston, MA: Shambhala, 1995; 86-87.

Mc Guffin, M et al, American Herbal Products Association's Botanical Safety handbook, Boca Raton, FL: CRC Press, 1997; 30-32, 79, 99 114.

Essential "Allergy Feedback Loop" Discovered by Hopkins Scientists, (author unknown) Press Release dated May 5, 1999.

* cited by examiner

ANTI-ALLERGY COMPOSITION AND RELATED METHOD

BACKGROUND OF THE INVENTION

This application claims benefit of U.S. Provisional Application No. 60/542,070, filed Feb. 5, 2004, which is hereby incorporated by reference.

The present invention relates to a composition and method for preventing and treating allergic reactions and diseases.

Many individuals are affected by allergy-related immunological disorders. Such disorders include, for example, bronchial asthma, allergic rhinitis (hay fever), and atopic dermatitis. Although these disorders have somewhat different effects on the body, they share a common allergic response, referred to as a type I, or immediate-type, anaphylactic allergic reaction. This response is mediated by substances, such as immunoglobin E (IgE) and histamines, and includes several steps.

In the first step of the reaction, referred to as the sensitization step, an immune response to an allergen is initiated upon exposure of a responsive individual to the allergen. This results in the generation of B cells that secrete allergen specific IgE. The IgE subsequently binds to IgE receptor sites on mast cells and basophils. In a second step, referred to as the degranulation step, when re-exposed to the allergen, the aforementioned receptor-bound IgE binds to the allergen resulting in degranulation of the mast cells and basophils. Degranulation releases a variety of vasoactive mediators, for example, histamines and proteases, which subsequently promote allergic and inflammatory responses. The third step, referred to as the inflammation step, is triggered by the mediators, and causes inflammatory cells to a) accumulate at sites of inflammation, for example, target organs, such as the lungs, and b) release chemicals, such as interleukin-3, interleukin-6, and macrophage colony stimulating factors. While inflammatory cells are normally activated to provide tissue defense, tissue maintenance and immunoregulation, in the case of allergies, activation of inflammatory cells serves to augment the allergic response.

Several allergic disease treatments exist. Many of these treatments use steroids to either inhibit the release of substances during the degranulation step, or inhibit the allergic reactions induced during the inflammation step. Although effective in mitigating allergic responses, these treatments are unhelpful in preventing the onset of the type I allergic reaction, that is, the treatments fail to inhibit IgE production, and accordingly fail to stop the underlying inflammatory process. A consequence of this is that the treatments also fail to prevent an often life-threatening reaction referred to as anaphylactic shock, which is triggered simply by the initiation of the type I allergic reaction. Further, many of drugs used to inhibit the degranulation and inflammation steps also have undesirable side effects. For example, degranulation is often treated with corticosteroids, and inflammation is frequently treated with glucocortosteroids; however, these drugs can cause numerous side effects, such as weight gain, water retention, hypertension, and increased cholesterol levels.

SUMMARY OF THE INVENTION

The aforementioned problems are overcome in the present invention which provides a composition and related method that inhibits or prevents an allergic response by down regulating the production of IgE, down regulating the binding of IgE antibodies to receptors on cells, and/or inhibiting histamine, prostoglandin $D_2$, or luekotriene $C_4$ release.

In one embodiment, the composition and method reduce and/or prevent the production of IgE antibodies. This can be accomplished by the composition preventing B cells of the responsive individual from secreting IgE antibodies.

In another embodiment, the composition and method reduces the level of IgE receptor sites on mast cells and basophils. This, in turn, can prevent the activation of the mast cells and/or basophils to release those mediator substances that promote allergic and subsequent inflammatory responses.

In a further embodiment, the composition and method inhibits or prevents the release of allergic response mediators, including histamine, prostoglandin $D_2$, and/or luekotriene $C_4$. Accordingly, cell degranulation can be prevented to prevent, inhibit or stop an allergic or inflammatory response.

In yet another embodiment, the composition can include at least one of the following ingredients: Perilla leaf (or Perilla seed), specifically the ingredient luteolin (from *Perilla fruteucens*), Cinnamon (*Cinnamon zeylanicum*), Kiwi extract (from *Actinidia arguta*), Picao preto (*Bidens pilosa*), Hesperidin (*Citrus senesis*), Acerola cherry (*Malphighia glabra*), Guaco (*Mikania glomerata*), Holy Basil (*Ocimum sanctum*), Kakadu (*Terminalia fernandida*), Solarnum (*Solanum xanthocarpum*), Kiwi juice (from *Actinidia chinensis*), Rosmarinic acid (from *Rosmarinus officinalis*), Tinospora (from *Tinospora cordifolia*), and Aframomum (from *Aframomum melegueta*). In a more specific embodiment, the composition can include: Cinnamon, Acerola and Picao preto. In an even more specific embodiment, the composition can include: Cinnamon, Acerola, Picao preto and at least one of luteolin, Tinospora, Rosmarinic acid, and Aframomum. These ingredients can be present in equal amounts. In another more specific embodiment, the composition can include: Cinnamon, Acerola, luteolin and at least one of Picao preto, Tinospora, Rosmarinic acid, and Aframomum. These ingredients can be present in equal amounts.

In a method of the present invention, the compositions above can be administered to cells and/or subjects to inhibit or prevent an allergic or inflammatory response by at least one of (a) down regulating the production of IgE, (b) down regulating the binding of IgE antibodies to receptors on cells, and/or (c) inhibiting or preventing the release of mediators such as histamine, $PGD_2$ and/or $LTC_4$.

In the method of the present invention, the compositions above can be administered in an effective amount to a subject undergoing an allergic response or disease or the potential for the same, for example, allergic rhinitis, bronchial asthma, allergic conjunctivitis, atopic dermatitis, food allergy, hyper IgE syndrome, anaphylactic shock, atopic eczema and rheumatoid arthritis. In one embodiment, the composition can be administered to lower IgE levels in a subject, for example, by down regulating the production of and/or binding of IgE antibodies to receptors on cells. In another embodiment, the composition can be administered to inhibit or prevent the release of allergic response mediators such as histamine, $PGD_2$ and/or $LTC_4$.

The present invention provides many benefits over many conventional anti-allergy treatments. For example, the composition and method can inhibit IgE production, and accordingly prevent or delay sensitization of mast cells and/or basophils, and the subsequent inflammatory process. Additionally, the use of ingredients optionally derived from fruit and herb sources in the composition can reduce the potential for adverse side effects for subjects using the composition.

Further, the composition can target both allergic responses upstream of most current anti-allergy treatments, which only block histamine action or prevent the production of anti-inflammatory mediators such as prostoglandins and leukotrienes, as well as inhibit or prevent release of the anti-inflammatory mediators. Accordingly, the present invention can mitigate and/or prevent the incidence of anaphylactic shock, which many other purely downstream treatments fail to do, as well as down regulate allergic response mediators.

DETAILED DESCRIPTION OF THE PREFERRED EMBODIMENT

I. Composition and Manufacture

Figure 1:
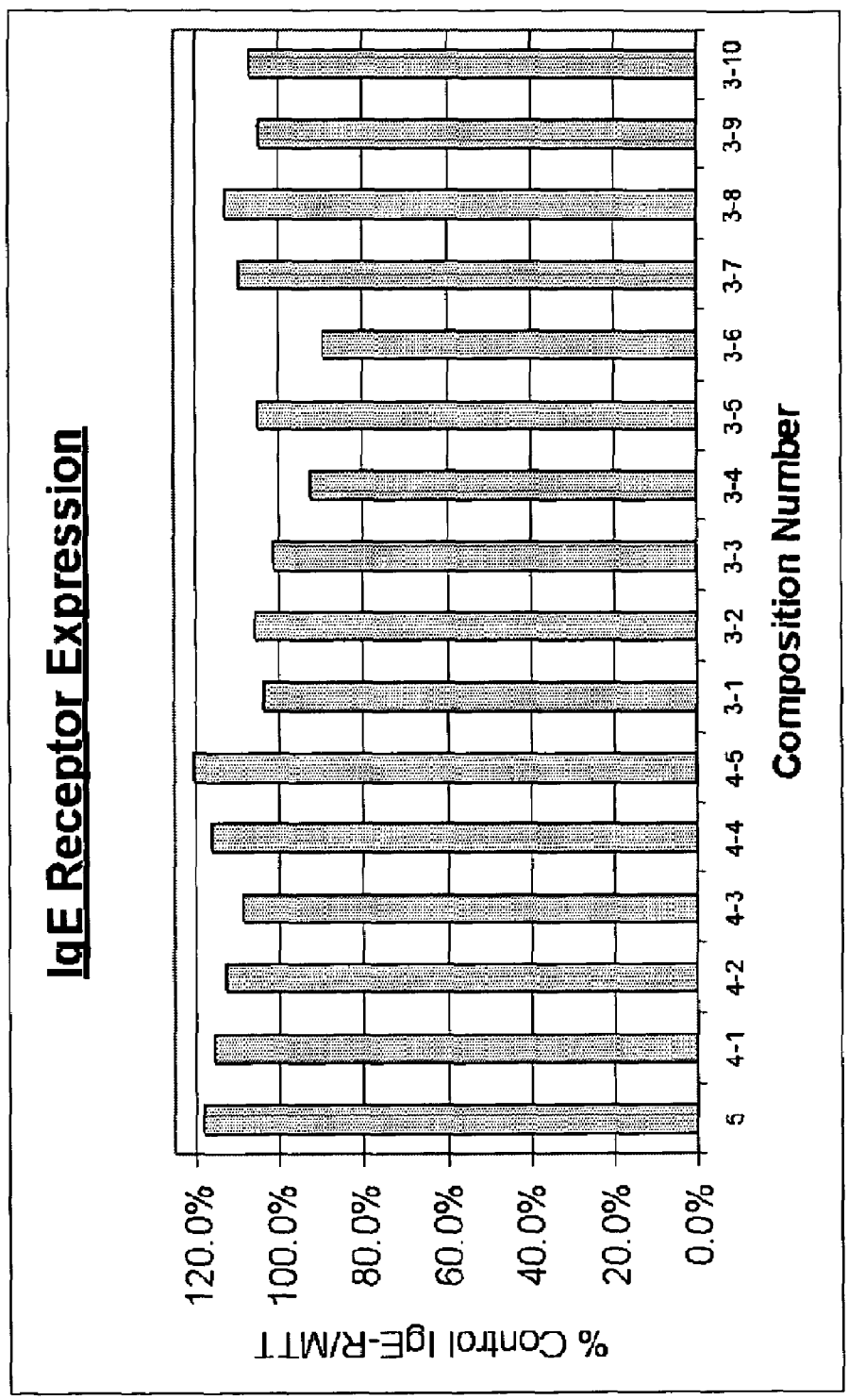
FIG. 1 is a graph illustrating the effect of the compositions of the present invention on IgE receptor expression.

The composition of the present invention can be prepared by mixing acceptable carriers with a mixture including effective amounts of at least one, at least two, at least three or at least four of the following ingredients: Perilla leaf or seed, specifically the ingredient luteolin (from *Perilla fruteucens*), Cinnamon (*Cinnamon zeylanicum*), Kiwi extract (from *Actinidia arguta*), Picao preto (*Bidens pilosa*), Hesperidin (*Citrus senesis*), Acerola cherry (*Malphighia glabra*), Guaco (*Mikania glomerata*), Holy Basil (*Ocimum sanctum*), Kakadu (*Terminalia fernandida*), Solarnum (*Solanum xanthocarpum*), Kiwi juice (from *Actinidia chinensis*), Rosmarinic acid (from *Rosmarinus officinalis*), Tinospora (from *Tinospora cordifolia*), Aframomum (from *Aframomum melegueta*), Tumeric, (*curcuma longa*), Cumaru (*Amburana cearensis*), Marigold (*Tagetes erecta*), Nettle Root (*Urtica dioica*), Quercetin (*Dimorphandra gardneriana*), Ginger (*Zingiber officinale*), Boswin 30 (*Borwellia serratta*), Trikartu extract (An *ayurvedic* extract composed of a third each of Pipli (*piper longum*), Black pepper (*piper nigrum*), Bioperine, available from Sabinsa Corp. of Piscataway, N.J., and Allergy Formula, available from Geni Herbs of Noblesville, Ind.

In one embodiment, the composition includes: Cinnamon, Acerola and Picao preto. Optionally, this composition further includes at least one of luteolin, Tinospora, Rosmarinic acid, and Aframomum. In another embodiment, the composition includes: Cinnamon, Acerola and luteolin. Optionally, this composition further includes at least one of Picao preto, Tinospora, Rosmarinic acid, and Aframomum. When multiple ingredients are included in the composition, the ingredients can be present in approximately equal amounts by weight of the composition. For example, a composition can include 10% by weight carriers, and 90% by weight IgE and/or mediator affecting ingredients. Where there are three ingredients in this exemplary composition, such as Cinnamon, Acerola and Picao preto, each of these ingredients may be present in amounts each equal to about 30% by weight of the composition.

Some ingredients of the composition perform better at affecting or otherwise inhibiting certain mechanisms in allergic and inflammatory responses. For example, some ingredients down regulate IgE via a specific mechanism. As a specific example, Kiwi extract operates extremely well to reduce IgE secretion, but moderately well at reducing IgE receptor expression. On the other hand, Cinnamon operates very well to reduce IgE receptor expression, but moderately well to reduce IgE secretion. Accordingly, some compositions of the present invention include both ingredients that reduce IgE receptor expression, and ingredients that reduce IgE secretion. These compositions therefore down regulate IgE via two mechanisms: by reducing IgE receptor expression and by reducing IgE secretion. As used herein, allergic response encompasses an inflammatory response, and inhibiting an allergic response includes, but is not limited to partial inhibition of the response, complete arrest of the response, and/or prevention of the response.

Furthermore, some ingredients additionally or alternatively inhibit the release of mediators better than other ingredients; and some ingredients inhibit the release of some mediators better than other mediators. As a specific example, Aframomum operates better than Cinnamon at inhibiting $LTC_4$ release, but Cinnamon outperforms Aframomum at inhibition of histamine release. Likewise, Aframomum operates very well to inhibit $LTC_4$ release, but only moderately well to inhibit histamine release. Moreover, some ingredients, for example Cinnamon, affect several mechanisms in the allergic response. As noted above, Cinnamon reduces IgE receptor expression, as well as inhibits the release of mediators such as histamine and $PGD_2$. The specific mechanisms by which the different ingredients and combinations of ingredients operate, as well as their relative efficacy, is discussed in further detail below.

Compositions that included specific combinations of ingredients also exhibited surprising and unexpected synergy in affecting certain mechanisms. For example, the combination of Cinnamon, Acerola and Picao preto, also referred to herein as the Blend, inhibited histamine release better than any one of these ingredients alone. As discussed in further detail below in Example 7, the Blend inhibited histamine release to 29% of the histamine release by cells untreated with the Blend or any other ingredient. In contrast, Cinnamon individually inhibited histamine release to 84%, Acerola to 70% and Picao preto to 96%. This result was interesting because a combination of ingredients does not frequently lead to such synergy and overall improvement in mechanism effect. For example, in Example 8, the Blend inhibited histamine release to 73% of that by untreated control cells, Aframomum inhibited histamine release to 96% of untreated control samples, but the combination of the Blend and Aframomum inhibited histamine release to 100% of untreated control samples. It is believed that the frequent non-synergistic effect of ingredient combinations is caused by the individual ingredients counteracting one another, and/or affecting different biological mechanisms, so that the net effect of the combination is less than, or is less desirable than, the effect of each ingredient alone.

For purposes of this disclosure, an effective amount of an ingredient or composition refers to the amount necessary to elicit the desired biological response. Additionally, as used herein, mast cell refers to at least one of mast cells, basophils, and other cells with IgE receptors. Further, the Ginger can be of a special variety, for example Ginger 5%, which means Ginger extract at 5% concentration. In one embodiment, the Kiwi extract used is of a special variety, referred to as PanGenomic A, which is available from PanGenomic Co., Ltd. of Seoul, Korea. The Hesperidin used can also be of a special variety, specifically Hesperidin 80%, which means Hesperidin extract at 80% concentration. In addition, the Tinospora used can be Tinospora present in the product sold under the trade name Tinofend, which is commercially available from Geni Herbs.

Effective amounts for particular embodiments of the composition when used in connection with in-vitro testing may vary as desired. In one embodiment, the composition includes a combination of the ingredients Cinnamon, Acerola and Picao preto, referred to herein as a Blend, with ranges of dosages for the Blend being greater than 1 µg/ml, with each ingredient of the Blend being present in equal concentrations.

In another embodiment, at least one of Luteolin, Aframomum, Rosmarinic acid, and Tinospora is added to the Blend. The Luteolin may be derived from Perilla seed and/or optionally, Perilla leaf. In this embodiment, the dosage range for the Luteolin may be greater than 1 µg/ml, the dosage range for the Aframomum may be greater than 1 µg/ml, the dosage range for the Rosmarinic acid may be greater than 1 µg/ml, and the dosage range for the Tinospora may be greater than 1 µg/ml.

Furthermore, effective amounts for particular embodiments of the composition when used in connection with in-vivo testing or regular subject administration may vary as desired. In one embodiment, the composition may include a combination of the ingredients Cinnamon, Acerola and Picao preto, i.e., the Blend, with ranges of daily subject dosages for the Blend being from about 1 mg to about 540 mg; about 1 mg to about 400 mg; about 1 mg to about 270 mg; about 270 mg to about 400 mg; or about 270 mg to about 540 mg. In this embodiment, each individual ingredient of the Blend may have ranges of daily subject dosages that are equal to that of the Blend ranges. The components of the Blend also can be expressed as a percent by weight of the total composition in which the Blend is incorporated. Specifically, Cinnamon can be present in a percent by weight in the ranges of: about 5% to about 50%; about 10% to about 25%; about 15% to about 22%; and about 20%. Acerola may be present in the amount by weight percent of: about 5% to about 50%; about 10% to about 25%; about 15% to about 22%; and about 20%. Picao preto may be present in a percent by weight in the ranges of: about 5% to about 50%; about 10% to about 25%; about 15% to about 22%; and about 20%. Other ranges may be used as desired.

In a more specific embodiment, at least one of Luteolin, Aframomum, Rosmarinic acid, and Tinospora can be added to the Blend. The Luteolin may be derived from Perilla seed and/or optionally, Perilla leaf. In this embodiment, the ranges of daily subject dosages for the Luteolin may be from about 1 mg to about 225 mg; about 1 mg to about 180 mg; about 1 mg to about 135 mg; about 135 mg to about 180 mg; or about 180 mg to about 225 mg. The ranges of daily subject dosages in this embodiment for the Aframomum or Rosmarinic acid may be from about 1 mg to about 300 mg; about 1 mg to about 225 mg; about 1 mg to about 150 mg; about 150 mg to about 225 mg; or about 225 mg to about 300 mg. The ranges of daily subject dosages in this embodiment for the Tinospora may be from about 1 mg to about 900 mg; about 1 mg to about 600 mg; about 1 mg to about 300 mg; about 300 mg to about 600 mg; or about 600 mg to about 900 mg.

In yet another embodiment, the composition may include a combination of the ingredient Cinnamon, Acerola and Luteolin, a combination which is also referred to as the Formula herein. The Luteolin may be derived from Perilla seed and/or optionally, Perilla leaf. Acceptable effective amounts for this embodiment when used in connection with in-vitro testing may vary as desired. An example of such a dosage range for the Formula is greater than 1 µg/ml, with each ingredient of the Formula being present in equal concentrations.

In another embodiment, at least one of Picao preto, Luteolin, Aframomum, Rosmarinic acid, and Tinospora is added to the Formula. In this embodiment, the dosage range for the Picao preto may be greater than 1 µg/ml, the dosage range for the Aframomum may be greater than 1 µg/ml, the dosage range for the Rosmarinic acid may be greater than 1 µg/ml, and the dosage range for the Tinospora may be greater than 1 µg/ml.

Acceptable ranges of daily subject dosages for the Formula are from about 1 mg to about 540 mg; about 1 mg to about 400 mg; about 1 mg to about 270 mg; about 270 mg to about 400 mg; or about 270 mg to about 540 mg. In this embodiment, each individual ingredient of the Formula may have ranges of daily subject dosages that are equal to that of the Formula ranges. In another example, the components of the Formula can be expressed as a percent by weight of the total composition in which the Formula is incorporated. In such an example, Cinnamon can be present in a percent by weight in the ranges of: about 5% to about 50%; about 10% to about 25%; about 15% to about 22%; and about 20%. Acerola may be present in the amount by weight percent of: about 5% to about 50%; about 10% to about 25%; about 15% to about 22%; and about 20%. Luteolin may be present in a percent by weight in the ranges of: about 5% to about 50%; about 10% to about 25%; about 15% to about 22%; and about 20%. Other ranges may be used as desired. In a more specific embodiment, at least one of Picao preto, Aframomum and Tinospora may be added to the Formula. The ranges of daily subject dosages for these ingredients may the same as that noted above in connection with the previous embodiment.

The composition of the present invention can be prepared in any manner that preserves the biological activity of the ingredients. Possible preparations of the composition include decoctions, aqueous extracts, organic solvent extracts, and dry powder. In one embodiment, the ingredients are dried and ground, and the resulting powder is processed into pill form, however, the composition can be processed into forms having varying delivery systems. For example, the ingredients can be processed and included in capsules, tablets, gel tabs, lozenges, strips, granules, powders, concentrates, solutions or suspensions. The ingredients can also be administered into the respiratory tract, e.g. in the treatment of asthma, anaphylactic or and other acute shock conditions via a spray, mist or aerosol. The ingredients also can be formulated, individually or in combination, with other foods to provide pre-measured nutritional supplements, supplemented foods, for example, single serving bars. In general, the composition can be administered to subjects orally, parenterally, rectally, intracisternally, intraperitoneally, topically and bucally.

The compositions of the present invention can include at least one acceptable excipient or carrier. For purposes of this disclosure, acceptable carrier means a non-toxic, inert solid, semi-solid or liquid filler, diluent, encapsulating material or formulation. Examples of acceptable carriers are the following: cellulose and its derivatives, such as sodium carboxymethyl cellulose, ethyl cellulose and cellulose acetate; starches, such as corn and potato starches; sugars, such as lactose, glucose, and sucrose; gelatin; talc; excipients, such as cocoa butter and waxes; oils, such as peanut oil, cottonseed oil, safflower oil, sesame oil, olive oil, corn oil, and soybean oil; glycols, such as propylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Other agents that can be present in the composition of the present invention include sweetening and flavoring agents, coating agents, lubricants, flow aids, coloring agents, releasing agents, perfuming agents, preservatives and antioxidants, as the application requires.

As a specific example of a delivery vehicle, preselected amounts of multiple ingredients, e.g., Cinnamon, Acerola and Picao preto in any of the ranges presented above, can be blended with excipients including microcrystalline cellulose silicified (a filler), stearic acid (a lubricant), and silicon dioxide (a flow aid). The blend can be filled into size #0 white capsules using a hand operated capsule filling machine, commercially available from T.M.P. of Milano, Italy. Such capsules can be administered to subjects according to a dosage regimen as desired.

II. Method of Use

The compositions of the present invention can be administered in a variety of ways. Specifically, the compositions can be administered to cells and/or a subject alone, or in combination with additional therapeutic treatments, such as corticosteroids, which are acceptable drugs for treating asthma. Moreover, the compositions can be administered with standard or reduced corticosteroid or other treatments. Further, the compositions can be administered in combination with other acceptable drugs use to treat allergies including, but not limited to, anti-histamines, non-steroidal anti-inflammatory drugs, steroidal anti-inflammatory drugs and decongestants.

In one embodiment, the compositions can be employed to treat existing allergic responses. For example, the compositions can be used to reduce the severity, intensity, and/or duration of an asthmatic response. In such an application, the compositions are administered to an individual after the individual develops the asthmatic symptoms. The compositions can also be administered to cells to test effect of the composition on an allergic response of the cells.

In an alternative or additional embodiment, the compositions can be used to prevent or delay the onset of a type I allergic reaction in an individual who has previously suffered such a reaction, or to prevent, reduce the severity, intensity, or duration of subsequently-developed symptoms. Optionally, where an antigen has been identified that is known to have induced, or at least is correlated with, the onset of previous allergic reactions, the compositions can be administered either before the onset of symptoms after a subsequent encounter with the antigen, or before the encounter.

In another alternative or additional embodiment, the compositions can be administered before the development of allergic sensitivity to a particular antigen. In this case, the compositions can be administered substantially concurrently with exposure to an antigen that has not previously been associated with an allergic reaction.

In general, the compositions of the present invention can be administered in an effective amount to cells or a subject having an allergic response or disease or the potential for the same, for example, allergic rhinitis, bronchial asthma, allergic conjunctivitis, atopic dermatitis, food allergy, hyper IgE syndrome, anaphylactic shock, atopic eczema and rheumatoid arthritis.

In one embodiment, the composition can be administered to inhibit an allergic response. This can be done by lowering IgE levels in cells or a subject, for example, by down regulating the production of and/or binding of IgE antibodies to receptors on cells. In turn, this is believed to prevent, mitigate and/or inhibit the sensitization step of a type I allergic reaction. By preventing, mitigating and/or inhibiting (all of which are encompassed by the term inhibiting as used herein) the onset of a type I allergic reaction, the subsequent reaction and resulting symptoms can also be prevented, mitigated and/or inhibited. These symptoms include but are not limited to hives, rashes, puritis, watery eyes, edema, diarrhea, bronchial constriction and/or inflammation, airway hyper-responsiveness, difficulty breathing, vasodilation, a decrease in blood pressure, increased IgE levels, increased plasma histamine levels, increased protease levels, anaphylaxis, and death.

In a further embodiment, the composition can be administered to cells or a subject to inhibit or prevent the release of allergic reaction mediators such as histamine, $PGD_2$ and/or $LTC_4$. In so doing, the type I allergic reaction, the subsequent reaction and resulting symptoms can also be inhibited.

III. Identification and Characterization of Compositions

A. IgE Testing and Results

The effects of the composition on IgE can be analyzed in any in-vivo or in-vitro model. In an exemplary in-vitro model, such testing was conducted by treating a basophilic cell line having cells with high levels of IgE receptors on their surfaces. After a predefined incubation period, the level of IgE secretion and IgE receptor expression was measured with immunochemical methods. The following examples describe how IgE secretion and IgE receptor expression was measured to identify and select combinations of ingredients having acceptable IgE down-regulating effect. Although Examples 1 and 3 describe ways to identify combinations of ingredients having IgE down-regulating effects, the methodologies set forth can also or alternatively be used to identify individual ingredients having IgE down-regulating effects, as illustrated in Examples 2, 4 and 5.

It is noted that the following examples are intended to illustrate certain particular embodiments of the invention, but are not intended to limit their scope, as defined by the claims.

EXAMPLE 1

Multiple combinations of composition ingredients, presented in Table I, were tested to determine the each of the combination's effectiveness in controlling IgE receptor expression. In each of the compositions of Table I, the ingredients are present in equal amounts. FIG. 1 demonstrates the effects of the compositions on IgE receptor expression.

TABLE I

Sample Composition Combinations of Ingredients

| 5 ingredients | 4 ingredients | | 3 ingredients | |
|---|---|---|---|---|
| Perilla seed | 4-1 | Perilla seed | 3-1 | Perilla seed |
| Hesperidin 80% | | Hesperidin 80% | | Hesperidin 80% |
| Picao preto | | Picao preto | | Picao preto |
| Kiwi extract | | Kiwi extract | 3-2 | Perilla seed |
| Cinnamomum | 4-2 | Perilla seed | | Hesperidin 80% |
| | | Hesperidin 80% | | Kiwi extract |
| | | Picao preto | 3-3 | Perilla seed |
| | | Cinnamomum | | Hesperidin 80% |
| | 4-3 | Perilla seed | | Cinnamomum |
| | | Hesperidin 80% | 3-4 | Perilla seed |
| | | Kiwi extract | | Picao preto |
| | | Cinnamomum | | Kiwi extract |
| | 4-4 | Perilla seed | 3-5 | Perilla seed |
| | | Picao preto | | Picao preto |
| | | Kiwi extract | | Cinnamomum |
| | | Cinnamomum | 3-6 | Perilla seed |
| | 4-5 | Hesperidin 80% | | Kiwi extract |
| | | Picao preto | | Cinnamomum |
| | | Kiwi extract | 3-7 | Hesperidin 80% |
| | | Cinnamomum | | Picao preto |
| | | | | Cinnamomum |
| | | | 3-8 | Picao preto |
| | | | | Kiwi extract |
| | | | | Cinnamomum |
| | | | 3-9 | Hesperidin 80% |
| | | | | Kiwi extract |
| | | | | Cinnamomum |
| | | | 3-10 | Hesperidin 80% |
| | | | | Picao preto |
| | | | | Kiwi extract |

Specifically, FIG. 1 presents the combination of ingredients, that is, the compositions, identified in Table I on the X-axis. The Y-axis depicts the data expressed as a percentage of tested IgE-R/MTT ("MTT" is 3-(4,5-Dimethylthiazol-2yl)-2,5-Diphenyltetrazolium bromide) to untreated control cells IgE-R/MTT. The control IgE-R/MTT is a calculation to normalize IgE receptor expression to cellular viability using well known and standard testing techniques.

As shown in FIG. 1, two compositions containing three ingredients, 3-4 and 3-6 appeared very effective. The ingredients of those compositions are Perilla seed, Picao preto, and Kiwi extract (3-4); and Perilla seed, Kiwi extract and Cinnamomum (3-6). It is surmised that the apparent increase in the IgE receptor expression in cells treated with 4 and 5 ingredients can be due to mild toxicity given the number of ingredients.

The methodology used to obtain the results of FIG. 1 will now be described. First, RBL-2H3 cells, available from ATCC (American Type Culture Collection) of Manassas, Va., were plated in 96 well plates at $3 \times 10^4$/well. Following adherence to the wells, the cells were exposed to the sample combinations of ingredients listed in Table I, each combination referred to as a "sample." Stock solutions of all samples were prepared in a solution of DMSO, ethanol, and water present in a ratio of 5:3:2 at 100 mg/ml. Each sample was then diluted to 100 μg/ml in media. Duplicate plates of each sample were prepared so that viability could be determined multiple times for each sample, with the results of the multiple samples averaged following treatment of the cells.

The plates were incubated an additional 48 hours. To measure IgE-receptor expression, the cells were fixed for 2 hours with 1% gluteraldehyde. Following fixation, the cells were washed twice with PBS-Tween 20 (0.01%), available from Aldrich of Milwaukee, Wis. Protein binding sites were blocked for 2 hours with 2% non-fat dry milk in PBS (Phosphate Buffer Saline buffered at pH 7.3). The cells were washed twice. The primary antibody, Rabbit anti-FcεRIα, available from Upstate Group, Inc., Lake Placid, N.Y., was added to the wells and diluted 1:4000 with 0.2% BSA (Bovine Serum Albumin). Following a 2 hour incubation, the wells were washed 5× with PBS-Tween 20 (0.01%) solutions. The secondary antibody, Goat anti-rabbit IgG-peroxidase, available from Sigma-Aldrich of St. Louis, Mo., was added to the wells at 1:20000 with 0.2% BSA.

Following a 1 hour incubation the wells were washed five times. 100 μliters (microliters) of TMB (3,3',5,5±Tetramethyl benzidine dihydrochloride) Substrate, available from Chemicon International of Temecula, Calif., was added to the wells. Subsequent color development was stopped by the addition of a sufficient amount, $H_2SO_4$ (for example, 100 μliters at 1 Normal).

For each of the multiple samples of the combination, the $OD_{450}$ (Optical Density measured at a wavelength of 450 nanometers) was read on a plate reader.

Continuing with a description of the methodology to obtain the data in FIG. 1, the viability of the cells was next determined by incubating the cells in the second plate with MTT in a concentration of 1 mg/ml for 3 hours. The reduced MTT was extracted with 70% isopropanol and the $OD_{540}$ (Optical Density at a wavelength of 540 nanometers) was read for each of the multiple samples.

Again, the vertical bars for each sample in FIG. 1 represent the ability of each sample, i.e., each composition, to control IgE receptor expression on the RBL-2H3 cells relative to IgE receptor expression on untreated RBL-2H3 cells. For example, the combination 3-4 exhibited an IgE receptor expression that was about 90% of the IgE receptor expression of the untreated or control cells. In other words, combination 3-4 decreased IgE receptor expression by about 10% from what that expression was in untreated control cells.

Figure 2:
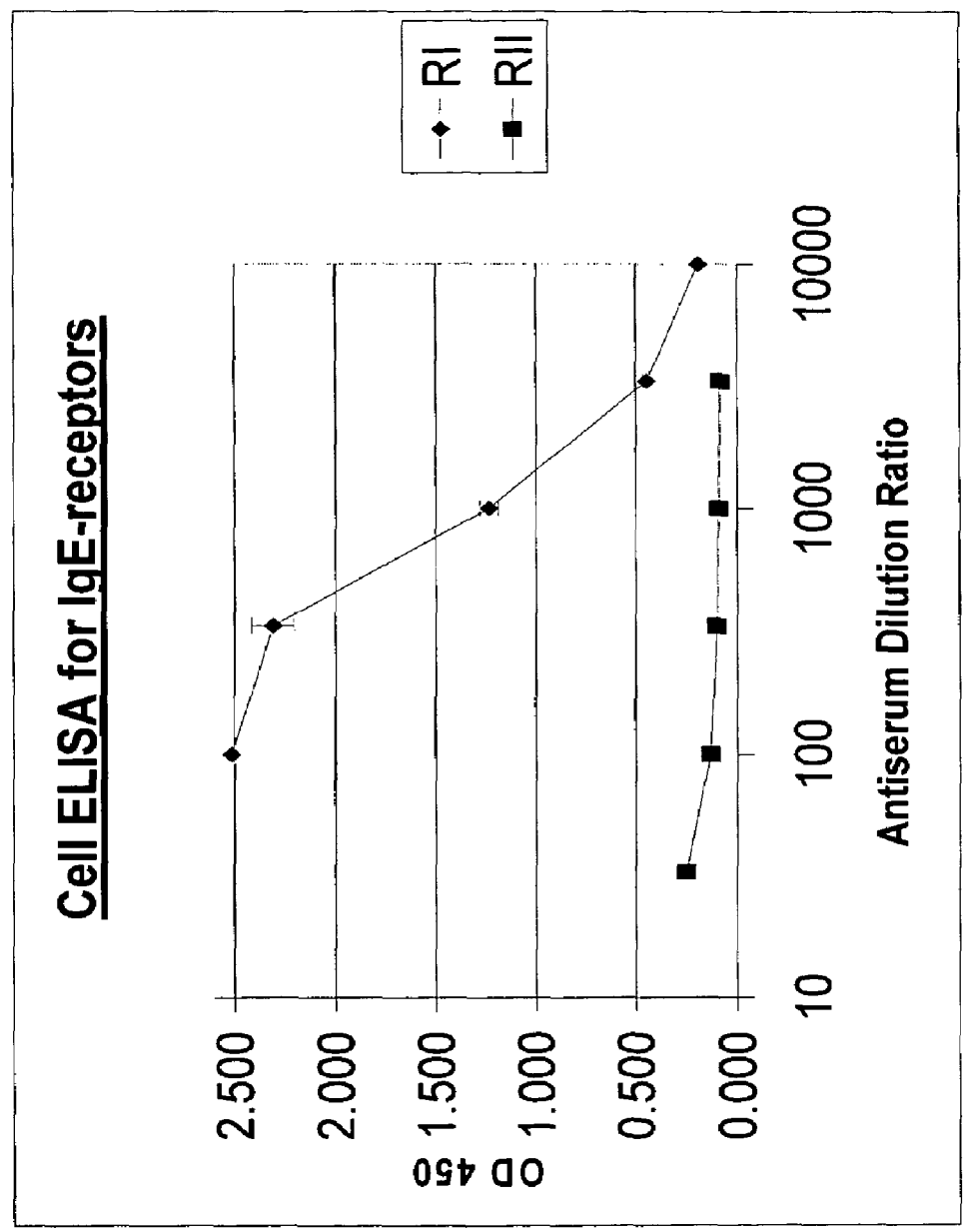
FIG. 2 is a graph illustrating the expression of different IgE receptors on test cells.

It is believed that the results of the testing on the RBL-2H3 cells in this example will be analogous to and/or indicative of the effect of the compositions on IgE receptor expression that would occur on mast cells within the body of a mammal, such as a human. This belief is derived from initial experiments, the results of which are illustrated in FIG. 2. There, the X-axis represents the $OD_{450}$ values, and the Y-axis represents the expression of type I and type II IgE receptors at varying dilutions. In particular, confirmation of IgE-RI, and not IgE-RII, expression on RBL-2H3 cells is shown in FIG. 2. Receptor expression was tested using the method described above with the rabbit anti-FcεRIIα antibody using antibody dilutions from 1:50 to 1:10000. The different dilutions of the antibody were used to optimize the experimental method. A mouse monoclonal antibody against anti-FcεRIIα antibody, available from Biodesign International of Saco, Me., was also used to test for the presence of IgE-RII (RII) on the cells, and the data in FIG. 2 show that levels of the type II (RII) receptor are negligible, but that the levels of type I receptor (RI) are significant. Because the type I receptor is the receptor that mediates degranulation of mast cells, there is a significant probability that the RBL-2H3 cells are appropriate for screening for the down-regulatory effect on IgE receptor expression. Accordingly, it is believed that those tested compositions having the ability to reduce IgE expression in the in-vitro testing above will be suitable for reducing IgE expression in animal subjects.

EXAMPLE 2

Multiple individual ingredients of the composition were tested to determine the effectiveness of each ingredient at controlling IgE receptor expression. Each of the individual ingredients in Tables II and III below were tested using the methodology presented above in connection with the combinations of ingredients in Example 1. The data expressed as Percent Control IgE Receptor/Viability denotes the level of IgE receptor expression of treated cells relative to untreated control cells in each experiment. The ingredients tested show different levels of satisfactory reductions in IgE receptor expression.

TABLE II

Effect of Individual Ingredients on IgE Receptor Expression

| Ingredient | Percent Control IgE Receptor/Viability |
| --- | --- |
| Perilla seed | 81% |
| Cinnamon | 86% |
| Picao preto | 91% |
| Hesperidin 80% | 90% |
| Guaco | 85% |
| Holy Basil | 87% |
| Kakadu concentrate | 83% |
| Solarnum | 85% |

In addition to the ingredients in Table II, other ingredients that can be used include Kiwi extract, Kiwi juice, and Acerola Cherry. The Holy Basil of Table II was obtained from GeniHerbs.

TABLE III

Effect of Individual Ingredients on IgE Receptor Expression

| Ingredient | Percent Control IgE Receptor/Viability |
| --- | --- |
| Cumaru | 91% |
| Marigold | 92% |
| Nettle Root | 91% |
| Tumeric | 89% |
| Allergy Formula | 83% |

In addition to the ingredients listed in Table III, other ingredients that can be used include Ginger PE 5%, Boswin 30, Trikartu extract, BioPerine, as well as those ingredients in Example 5 below.

EXAMPLE 3

Figure 3:
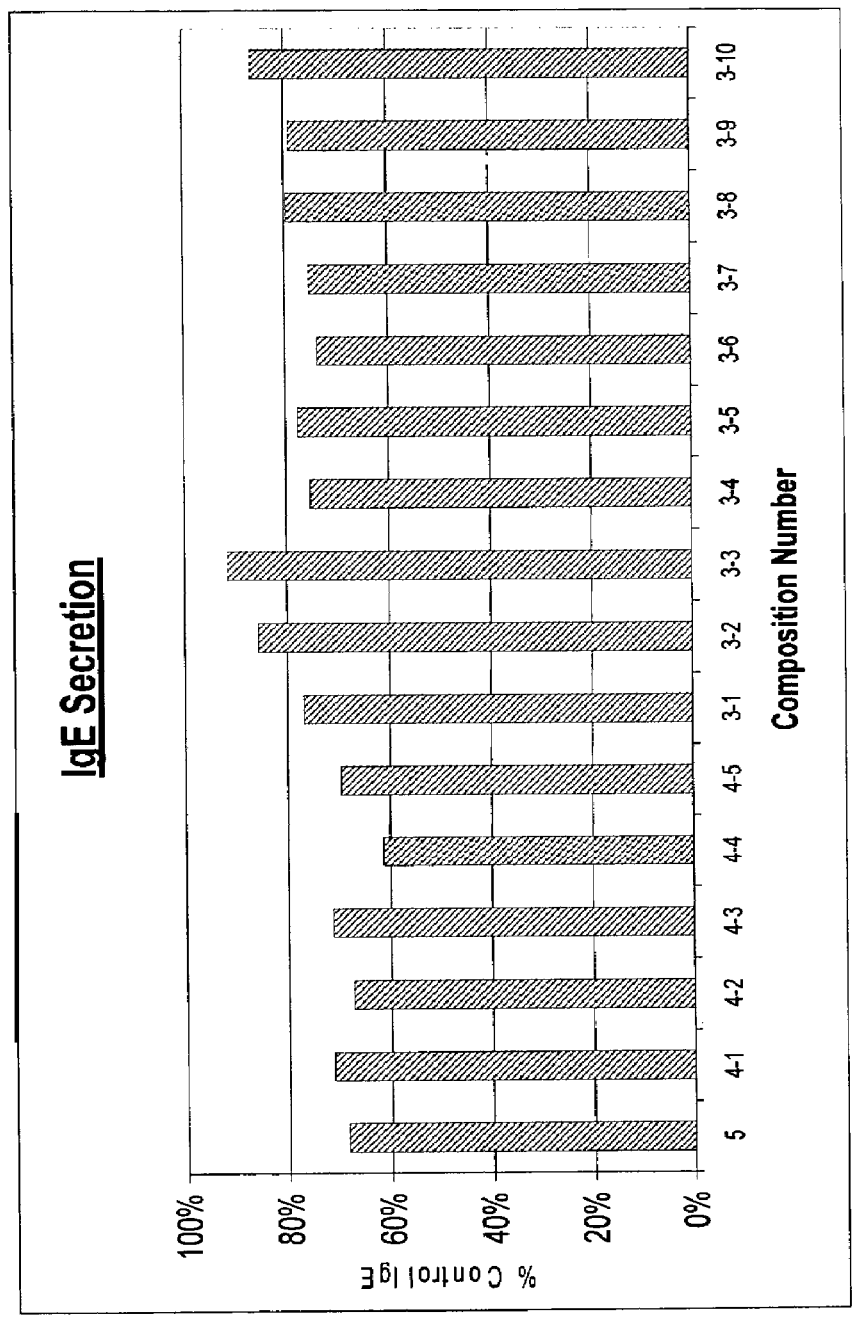
FIG. 3 is a graph illustrating the effect of the compositions on IgE secretion.

Multiple combinations of ingredients presented in Table II above were tested to determine the combinations effectiveness in controlling IgE secretion by cells. FIG. 3 demonstrates the effects of the composition combinations on IgE secretion by cells relative to IgE secretion of cells untreated with the compositions. Specifically, FIG. 3 presents the combination of ingredients, that is, the compositions, identified in Table I on the X-axis. The Y-axis depicts the data expressed as a percentage of the levels of IgE secreted by control cells, that is cells to which no compositions were added.

As shown in FIG. 3, the most effective compositions were 3-1, 3-4, 3-5, 3-6 and 3-7. Those compositions comprise: Perilla seed, Hesperidin 80%, and Picao preto (3-1); Perilla seed, Picao preto, and Kiwi extract (3-4); Perilla seed, Picao preto, and Cinnamomum (3-5); Perilla seed, Kiwi extract, and Cinnamomum (3-6); Heperidin 80%, Picao preto and Cinnamomum (3-7). As evident in FIG. 3, the compositions with 4 or 5 ingredients also appear to inhibit IgE secretion. It is believed that this can be the result of mild toxicity due to multiple ingredients.

The methodology used to obtain the results of FIG. 3 will now be described. First, U266 human myeloma cells, available from ATCC of Manassas, Va. were plated in 96 well plates at $4\times10^4$/well. The cells were exposed to the sample combinations of ingredients listed in Table I, each combination referred to as a "sample." Stock solutions of all samples were prepared in a solution of DMSO, ethanol, and water present in a ratio of 5:3:2 at 100 mg/ml. Each sample was then diluted to 100 µg/ml in media. Duplicate plates of each sample were prepared so that viability could be determined multiple times for each sample, with the results of the multiple samples averaged following treatment of the cells.

Figure 4:
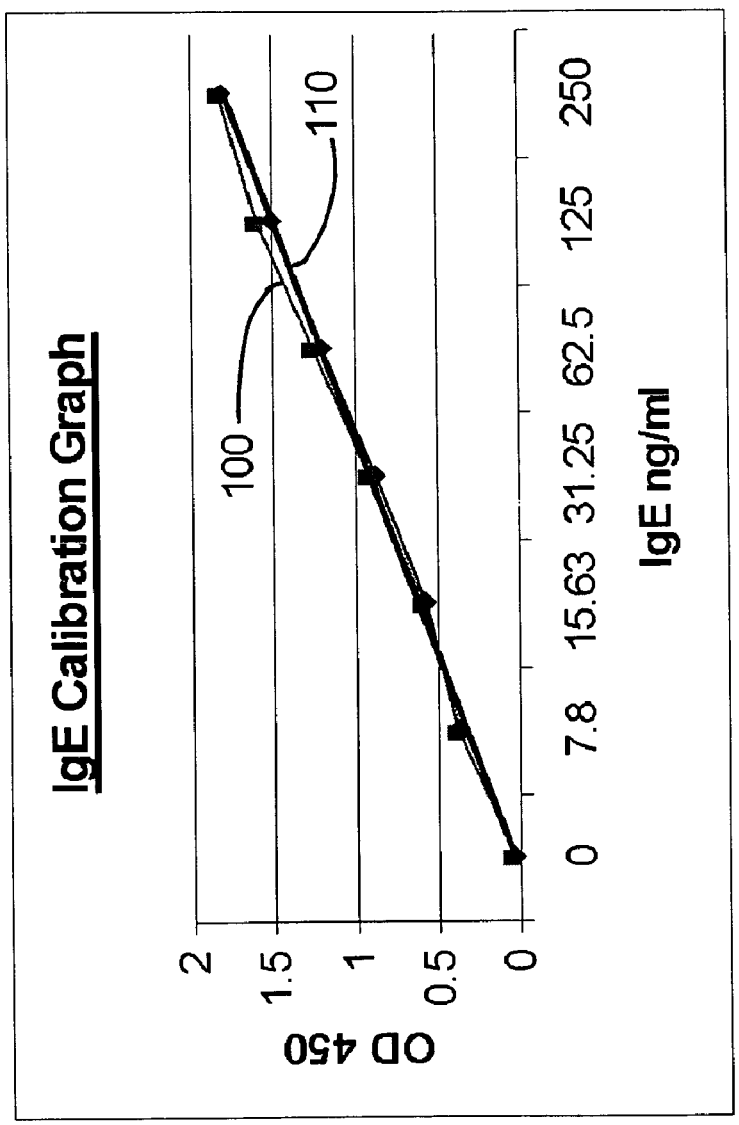
FIG. 4 is a graph illustrating a calibration curve used to extrapolate IgE concentration from the optical density data of composition samples.

The plates were incubated an additional 48 hours. Thereafter, the amount of IgE in the supernatants was measured using a conventional quantitative IgE ELISA kit available from Bethyl Laboratories of Montgomery, Texas. Next, the measured OD450 data from the IgE ELISA was inputted into a calibration graph, illustrated in FIG. 4, to determine the concentration of IgE in ng/ml in each supernatant. This calibration graph was generated by measuring the OD450 of multiple, known concentrations (in nanograms per ml) of purified IgE. As shown in the graph, the X-axis indicates the concentrations of the IgE in ng/ml; and the Y-axis indicates the OD450 derived from each of the concentrations. The line 100 connects the data points, while line 110 is a trend line corresponding to the equation in this particular embodiment of:

$$Y=0.2909X-0.2527 \qquad \text{Equation 1}$$

With the IgE calibration graph, the amount of IgE for each sample was determined, and the subsequent data was input into FIG. 3 for comparative analysis.

It is believed that the effect of the compositions in Table 1 on IgE secretion of U266 human myeloma cells is analogous to and indicative of the effect of those compositions on human or animal cells in-vivo due to the similar cellular structure and allergic reaction of the test cells and in-vivo cells.

EXAMPLE 4

Multiple individual ingredients of the composition were tested to determine their ability to down regulate IgE receptor expression and the secretion of IgE antibodies. These ingredients were Acerola cherry extract, Kiwi juice extract, Vitamin C and Holy Basil at varying concentrations. The Acerola extract and Vitamin C were obtained from Nutrilite of Lakeview, Calif.; and the Kiwi juice and Holy Basil were obtained from P.L. Thomas & Co., Inc. of Morristown, N.J.

Figure 5:
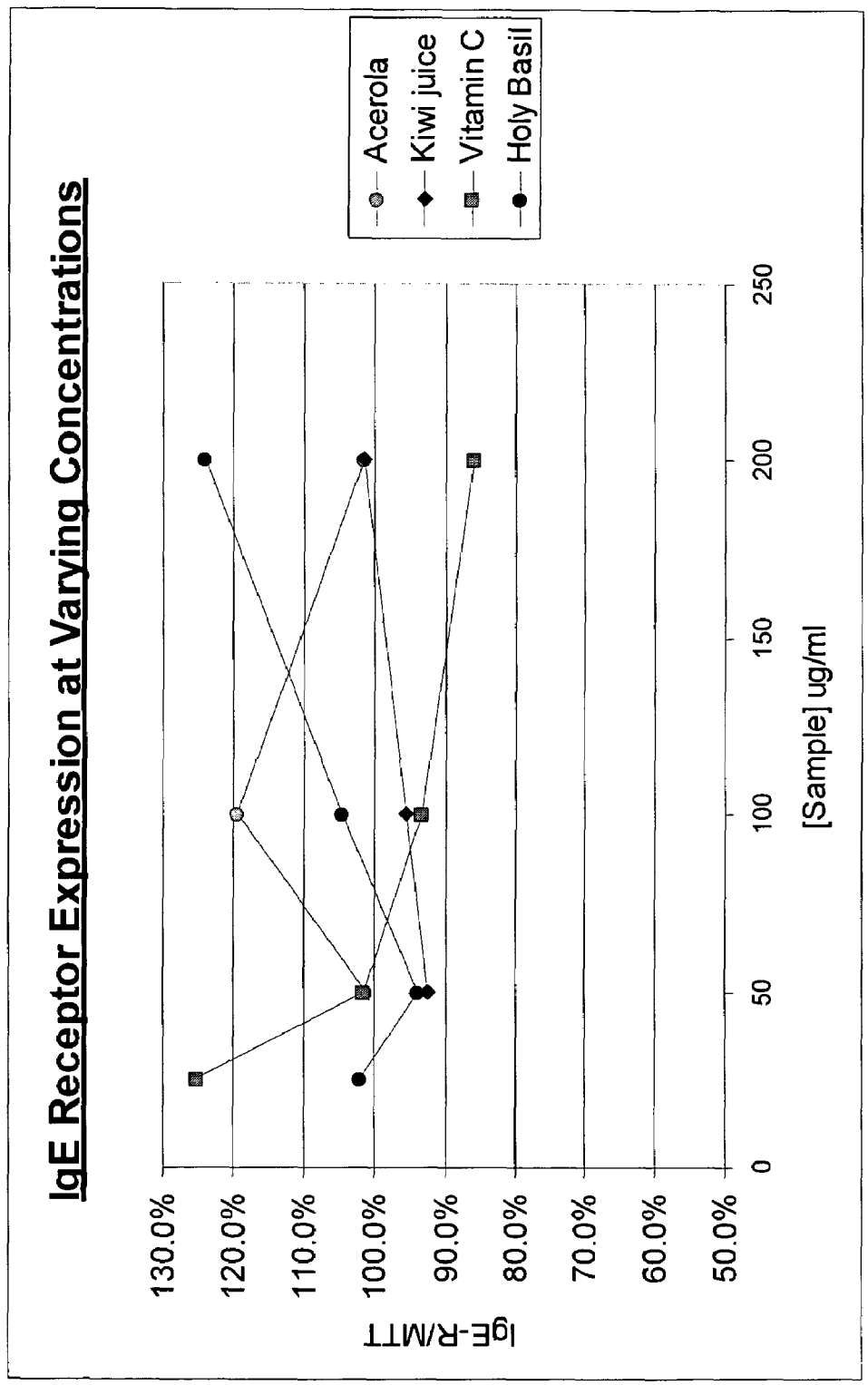
FIG. 5 is a graph illustrating the effect of individual ingredient compositions at varying concentrations on IgE receptor expression.

The data from this example demonstrate the effects of the different ingredients (samples) at varying concentrations on IgE receptor expression as illustrated in FIG. 5. As shown there, Vitamin C had a significant effect on IgE receptor expression. At 200 micrograms per milliliter, Vitamin C induced a 15% decrease in IgE receptor expression. The results illustrated in FIG. 5 were obtained using the same methodology as set forth above in Example 1, except that the concentration of each ingredient was varied as shown along the X-axis of FIG. 5.

Figure 6:
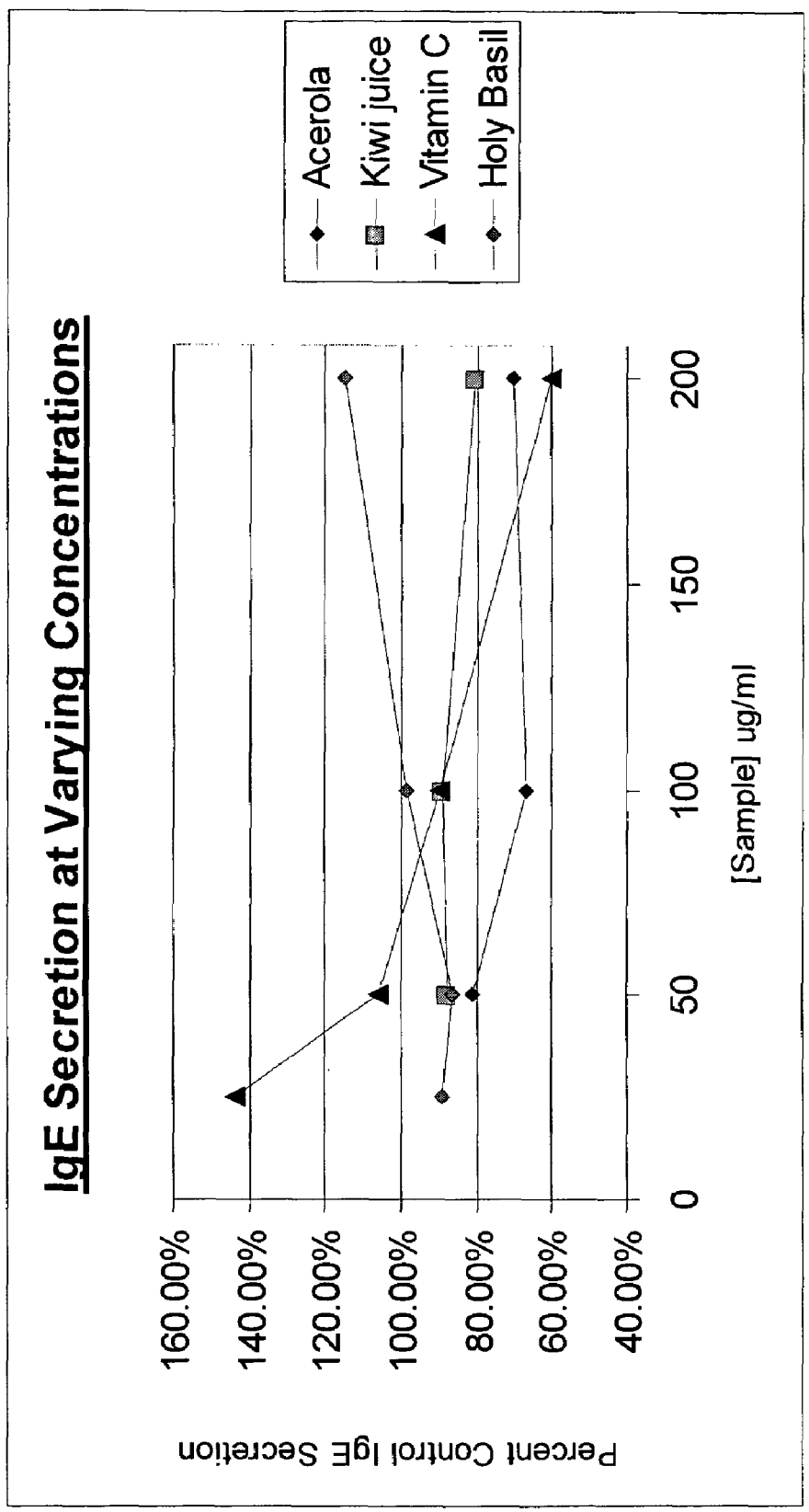
FIG. 6 is a graph illustrating the effect of individual ingredient compositions at varying concentrations on IgE secretion.

The data in FIG. 6 is representative of the effect of the various ingredients on inhibiting IgE secretion. The data are expressed as percent control of IgE secreted by treated cells relative to untreated control cells. As demonstrated in FIG. 6, Acerola extract, Kiwi juice, Vitamin C and Holy Basil all inhibited IgE secretion in the amounts shown. Acerola extract was the most potent at inhibiting IgE secretion. The results illustrated in FIG. 6 were obtained using the same methodology as set forth in Example 3, except that the concentration of each ingredient was varied as indicated on the X-axis of FIG. 6.

EXAMPLE 5

Multiple individual ingredients of the composition were tested to determine the effectiveness of each ingredient at controlling IgE receptor expression. Each of the individual ingredients in Table IV below were tested using the methodology presented above in connection with the combinations of ingredients in Example 1. The data expressed as Percent Control IgE-Receptor denotes the level of IgE receptor expression of treated cells relative to untreated control cells in each experiment. The ingredients tested show different levels of satisfactory reductions in IgE receptor expression.

TABLE IV

Effect of Ingredients on IgE Receptor Expression

| Ingredient | Ingredient Concentration | Percent Control IgE-Receptor |
|---|---|---|
| Luteolin | 100 µg/ml | 82 |
| Cinnamomum | 100 µg/ml | 86 |
| Acerola | 100 µg/ml | 107 |
| Tinospora | 100 µg/ml | 109 |

Figure 7:
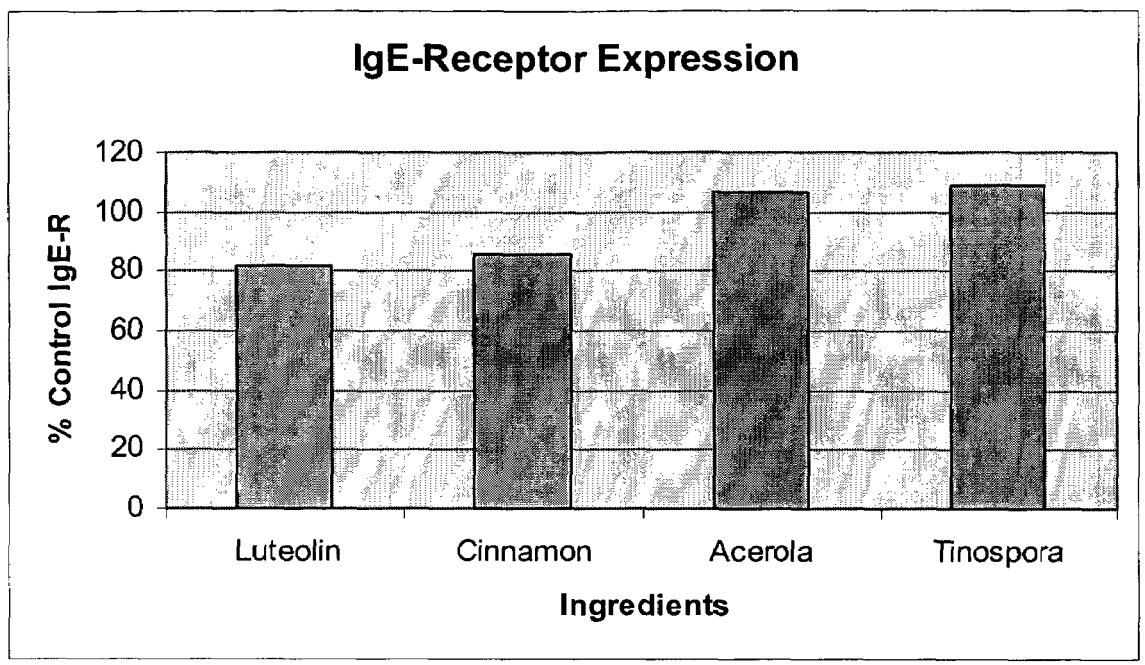
FIG. 7 is a graph illustrating the effect of the ingredient compositions on IgE receptor expression.

The data from Table IV is illustrated in FIG. 7 to graphically demonstrate the effects of the different ingredients. As shown there, luteolin from Perilla leaf and Cinnamon both had a significant effect on IgE receptor expression.

EXAMPLE 6

Multiple individual ingredients, as well as the Blend (which includes equal parts Cinnamon, Acerola and Picao) were tested to determine the effectiveness of each at controlling IgE secretion using the methodology presented above in connection with the ingredients in Example 3. The data in Table V expressed as Percent Control IgE Secretion denotes the level of IgE secretion by treated cells relative to untreated control cells in each experiment. The ingredients tested show different levels of satisfactory reductions in IgE secretion.

TABLE V

Effect of Ingredients on IgE Secretion

| Ingredient | Ingredient Concentration | Percent Control IgE-Secretion |
|---|---|---|
| Luteolin | 100 µg/ml | 53 |
| Acerola | 100 µg/ml | 60 |
| Butterbur | 100 µg/ml | 71 |
| Blend | 100 µg/ml | 73 |
| Tinospora | 100 µg/ml | 77 |
| Picao | 100 µg/ml | 89 |
| Cinnamon | 100 µg/ml | 94 |

Figure 8:
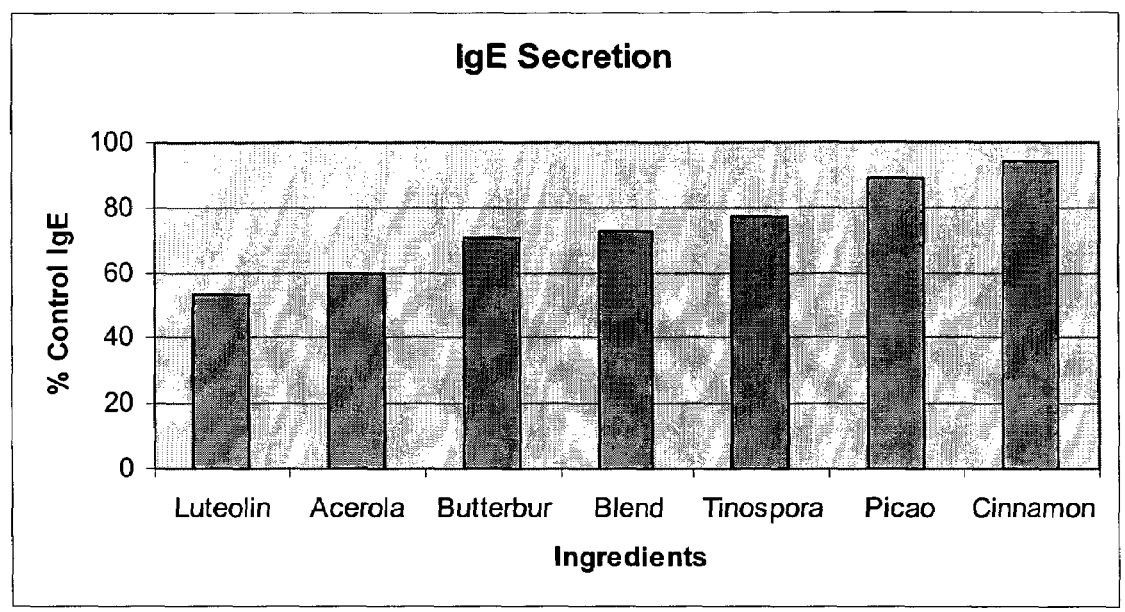
FIG. 8 is a graph illustrating the effect of the ingredient compositions on IgE secretion.

The data from Table V is illustrated in FIG. 8 to graphically demonstrate the effects of the different ingredients. As shown there, most of the individual ingredients, as well as the Blend had a significant effect on IgE secretion.

B. Allergy Mediator Testing and Results

The effects of the composition on allergy mediator release can be analyzed in any in-vivo or in-vitro model. In an exemplary in-vitro model, allergy mediator release was assessed following exposure of mast cells to the composition as well as individual ingredients of the composition. The cells were sensitized and stimulated to cause degranulation. After a predefined incubation period, the levels of allergy mediators were measured with immunochemical methods. The following examples describe how mediator release was measured to identify and select combinations of ingredients having acceptable mediator release inhibition. The methodologies set forth in the following examples can be used to identify individual ingredients and combinations of ingredients that have an effect on mediator release. As an additional consideration, selection of individual ingredients and combinations of ingredients for the composition can be based on the ingredients' or combinations' ability to affect mediator release, as well as the ability to down regulate IgE. Indeed, those ingredients or combinations of ingredients that perform well at both mediator release and IgE down regulation are well suited for the treatment of allergic responses.

EXAMPLE 7

Multiple ingredients and combinations of ingredients of the composition presented in Table VI were tested to determine the effectiveness of each in inhibiting allergy mediator release. The mediators tested were histamine, $PGD_2$ and $LTC_4$. The concentration of each ingredient or combination for each mediator is also presented in the table. For example, the concentration of Rosmarinic acid when testing histamine was 10 nanograms per milliliter, when testing $PGD_2$ was 1 microgram per milliliter, when testing $LTC_4$ was 0.1 micrograms per milliliter.

TABLE VI

Effect of Ingredients on Allergy Mediator Release

| Ingredient | Ingredient Conc. for Histamine | Percent Control of Histamine Release | Ingredient Conc. for $PGD_2$ | Percent Control of $PGD_2$ Release | Ingredient Conc. For $LTC_4$ | Percent Control $LTC_4$ Release |
|---|---|---|---|---|---|---|
| Rosmarinic acid | 10 ng/ml | 9.3 | 1 µg/ml | 94 | 0.1 µg/ml | 120 |
| Tinospora | 100 ng/ml | 10 | 10 µg/ml | 94 | 1 µg/ml | 75 |
| Blend | 100 ng/ml | 29 | 10 µg/ml | 102 | 1 µg/ml | 56 |

TABLE VI-continued

Effect of Ingredients on Allergy Mediator Release

| Ingredient | Ingredient Conc. for Histamine | Percent Control of Histamine Release | Ingredient Conc. for PGD$_2$ | Percent Control of PGD$_2$ Release | Ingredient Conc. For LTC$_4$ | Percent Control LTC$_4$ Release |
|---|---|---|---|---|---|---|
| Luteolin | 100 ng/ml | 10 | 10 µg/ml | 68 | 1 µg/ml | 157 |
| Aframomum | 100 ng/ml | 24 | 10 µg/ml | 68 | 1 µg/ml | 88 |
| Acerola | 1 µg/ml | 70 | 0.1 µg/ml | 70 | 10 µg/ml | 63 |
| Cinnamon | 1 µg/ml | 84 | 0.1 µg/ml | 84 | 10 µg/ml | 60 |
| Picao preto | 1 µg/ml | 96 | N/A | N/A | N/A | N/A |

Figure 9:
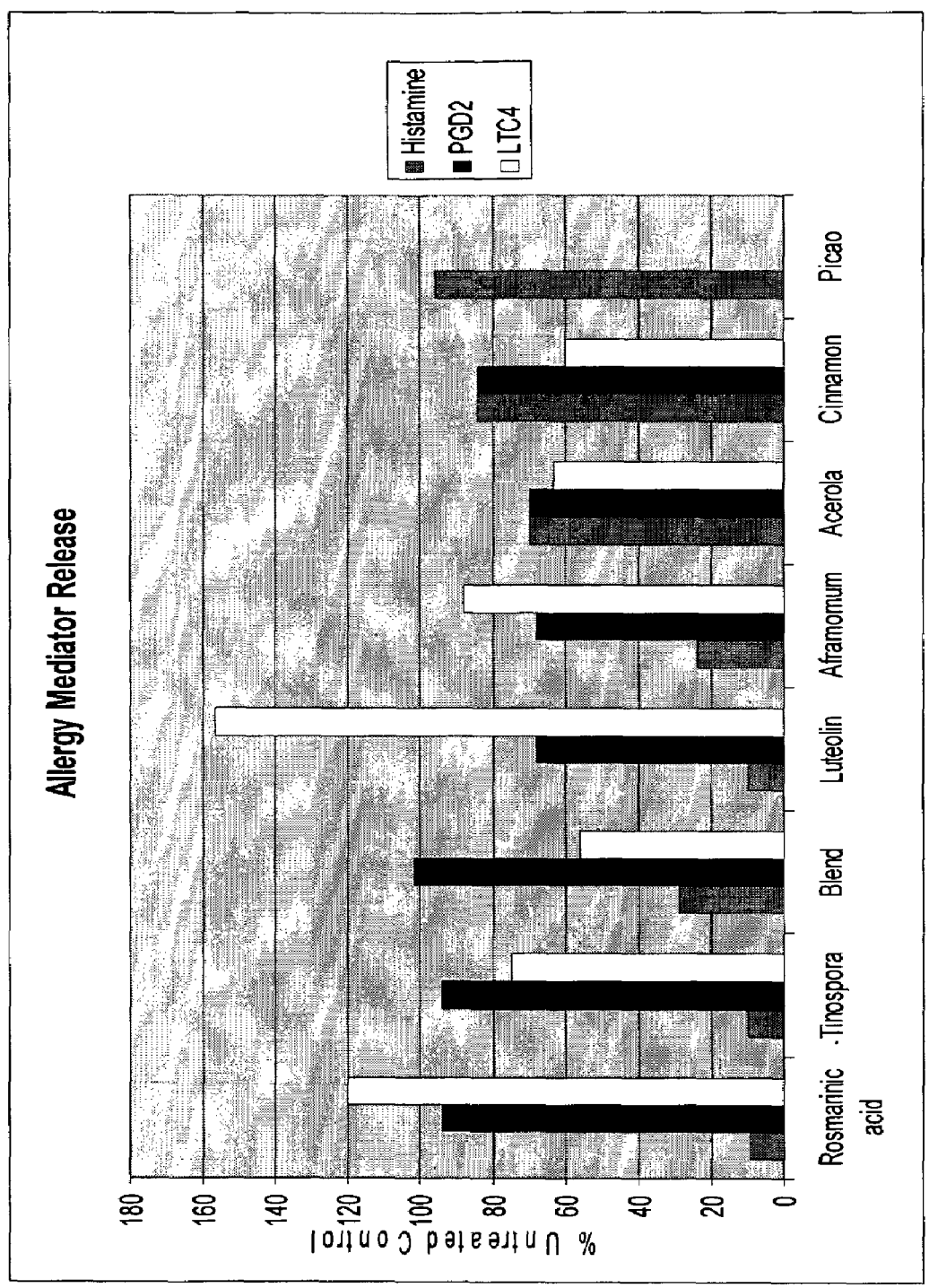
FIG. 9 is a graph illustrating the effect of the ingredient compositions on allergy mediator release.

The data from Table VI is illustrated in FIG. 9 to graphically demonstrate the effects of the different ingredients on allergy mediator release. As shown there, most of the individual ingredients, as well as the Blend had a significant effect on mediator release. Moreover, an unexpected synergy was observed when certain ingredients were combined. For example, when Cinnamon, Acerola and Picao preto were combined to form the Blend, the Blend inhibited histamine release to 29% of the histamine release that occurred in untreated cells. In contrast, Cinnamon individually inhibited histamine release to 84%, Acerola to 70% and Picao preto to 96%.

The methodology used to obtain the results of FIG. 9 will now be described. First, RBL-2H3 cells, available from ATCC (American Type Culture Collection) of Manassas, Va., were plated in 24 well plates at 5×10$^4$/well. Following adherence, the cells were exposed to the ingredients or combination of ingredients noted in FIG. 9, also referred to as samples. The samples were used at the concentrations noted in Table VI. Stock solutions of all samples were prepared in a solution of DMSO, ethanol, and water present in a ratio of 5:3:2 at 100 mg/ml. Each sample was then diluted in media to the final concentration. The cells were then incubated overnight with the samples. The following day a mouse anti-dinitrophenyl (DNP) IgE antibody, available from Sigma of St. Louis, Mo., was added to the cells at a final concentration of 1 ng/ml. The cells were incubated for 1.5 hr at 37° C. to allow binding of the IgE molecule to the cellular IgE receptor via the constant region of the antibody.

Following this incubation period, the cells were washed twice. A solution containing DNP conjugated to BSA (DNP-BSA), available from Calbiochem of San Diego, Calif., was added to the cells at 0.5 ng/ml. The cells were incubated an additional 1 hr at 37° C. The supernatants were assayed for the presence of histamine, PGD$_2$ and/or LTC$_4$ using ELISA kits commercially available from Cayman Chemical of Ann Arbor, Michigan according to the manufacturer's specifications.

Figure 10:
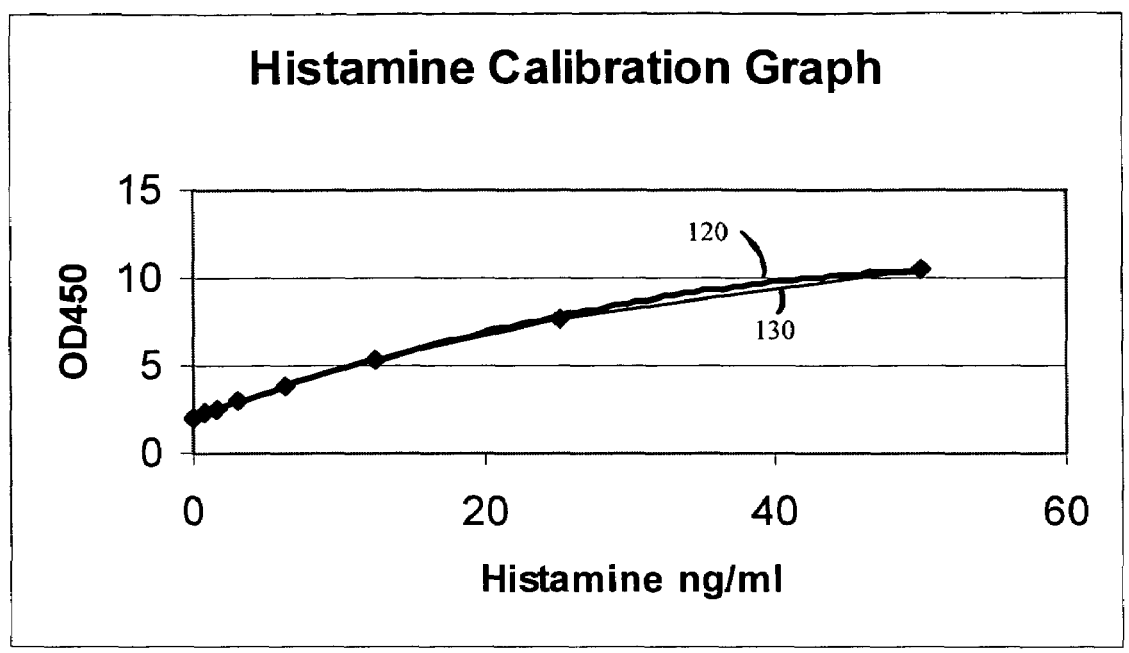
FIG. 10 is a graph illustrating a calibration curve used to extrapolate histamine release from the optical density data of composition samples.

Next, the measured OD450 data from the ELISA was inputted into a calibration graph to determine the amount by which histamine was reduced relative to an untreated control sample. An example of a histamine calibration graph is illustrated in FIG. 10. Suffice it to say that calibration graphs for PGD$_2$ and LTC$_4$ are similar. The calibration graph in FIG. 10 was generated by measuring the OD450 of multiple, known concentrations of purified histamine. As shown in the graph, the X-axis indicates the concentrations of the histamine in nanomolar; and the Y-axis indicates the OD450 derived from each of the concentrations. The line 120 connects the data points, while line 130 is a trend line corresponding to the equation in this particular embodiment of:

$$Y=-0.0025X^2+0.2915X+2.0775 \quad \text{Equation 2}$$

With the histamine calibration graph, the amount of histamine for each sample was determined, and the subsequent data was input into Table VI and FIG. 9 for comparative analysis.

It is believed that the effect of the compositions in this example, as well as Examples 8 and 9, on allergy mediator release is analogous to and indicative of the effect of those compositions on human or animal cells in-vivo due to the similar cellular structure and allergic reaction of the test cells and in-vivo cells.

EXAMPLE 8

Multiple ingredients and combinations of ingredients of the composition presented in Table VII were tested to determine the effectiveness of each in inhibiting allergy mediator release. The mediator tested was histamine. The concentration of each ingredient or combination tested was 10 nanograms per milliliter. For the Blend, the concentration of the individual ingredients was equal, for example, Cinnamon was 3.33 ng/ml, of Acerola was 3.33 ng/ml and for Picao preto was 3.33 ng/ml. Nothing was added to the control. Where ingredients were combined, each was present in an equal amount. For example, where the Blend was combined with Luteolin, both were present in equal amounts, that is, the Blend was present in a concentration of 10 ng/ml, and Luteolin at 10 ng/ml.

TABLE VII

Effect of Ingredients on Histamine Release

| Ingredient | Ingredient Concentration | Percent Control of Histamine Release |
|---|---|---|
| Rosemary | 10 ng/ml | 76.7% |
| Aframomum | 10 ng/ml | 95.6% |
| Tinospora | 10 ng/ml | 95.0% |
| Luteolin | 10 ng/ml | 88.1% |
| Butterbur | 10 ng/ml | 74.6% |
| Control | 10 ng/ml | 100.0% |
| Blend | 10 ng/ml | 72.8% |
| Blend + Rosemary | 10 ng/ml | 99.8% |
| Blend + Butterbur | 10 ng/ml | 105.7% |
| Blend + Aframomum | 10 ng/ml | 99.9% |
| Blend + Tinospora | 10 ng/ml | 78.0% |
| Blend + Luteolin | 10 ng/ml | 58.4% |
| Tinospora + Rosemary | 10 ng/ml | 82.4% |
| Tinospora + Luteolin | 10 ng/ml | 72.2% |
| Luteolin + Butterbur | 10 ng/ml | 75.3% |
| Tinospora + Aframomum | 10 ng/ml | 88.3% |
| Tinospora + Butterbur | 10 ng/ml | 93.9% |
| Luteolin + Aframomum | 10 ng/ml | 93.0% |
| Butterbur + Aframomum | 10 ng/ml | 73.8% |

Select data from Table VII is illustrated in FIGS. 11-14 to graphically demonstrate the effects of the different ingredients on histamine release, as well as demonstrate the effect on histamine release when certain ingredients are combined. The methodology used to produce the information of Table VII is identical to that in Example 7.

Figure 11:
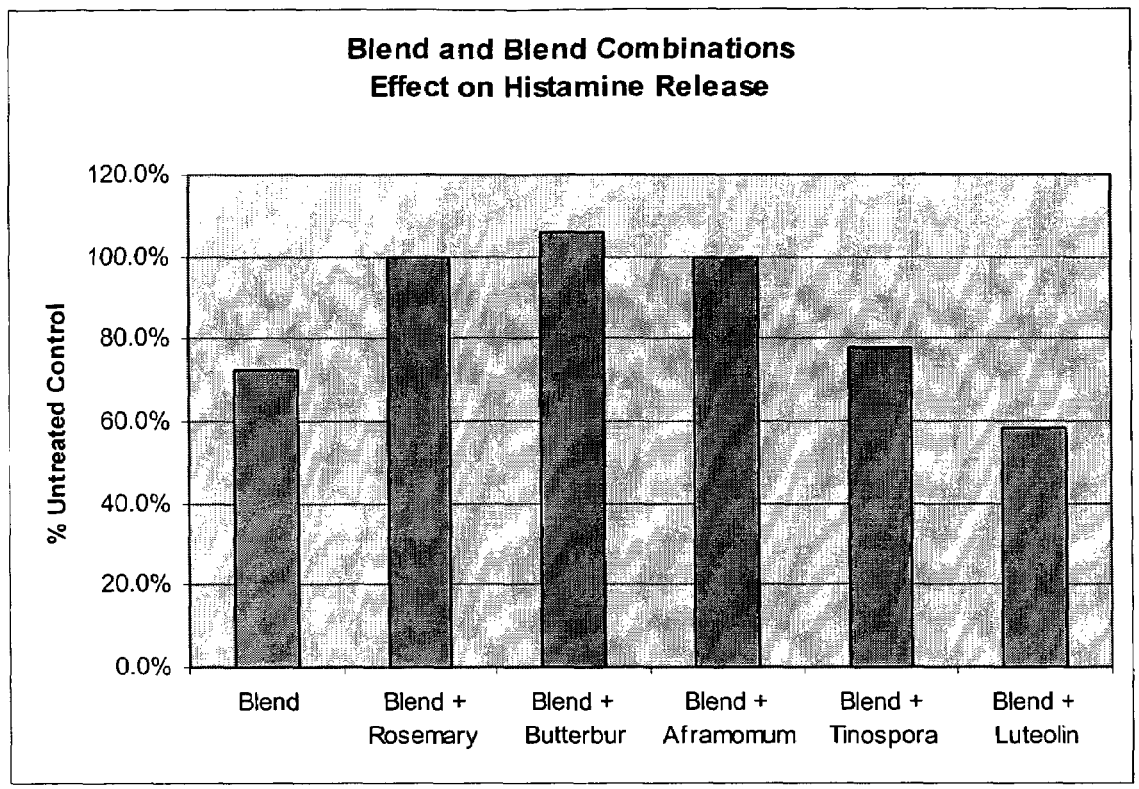
FIGS. 11-13 are graphs illustrating the effect of a multiple ingredient compositions on mediator release.

As shown in the Table and FIGS. 11-14, most of the individual ingredients, as well as the Blend had a significant effect on mediator release. Moreover, further unexpected synergy (in addition to that observed with the Blend) was observed when certain ingredients were combined. For example, as shown in FIG. 11, the combination of the Blend with luteolin inhibits histamine release to about 58% as compared to an untreated control, whereas individually luteolin from Perilla leaf inhibits to about 88%, and the Blend to about 73%. Further, the combination of the Blend with tinospora inhibits histamine release to about 78%, whereas individually the Blend inhibits histamine release to about 73% and tinospora to about 95%.

Figure 12:
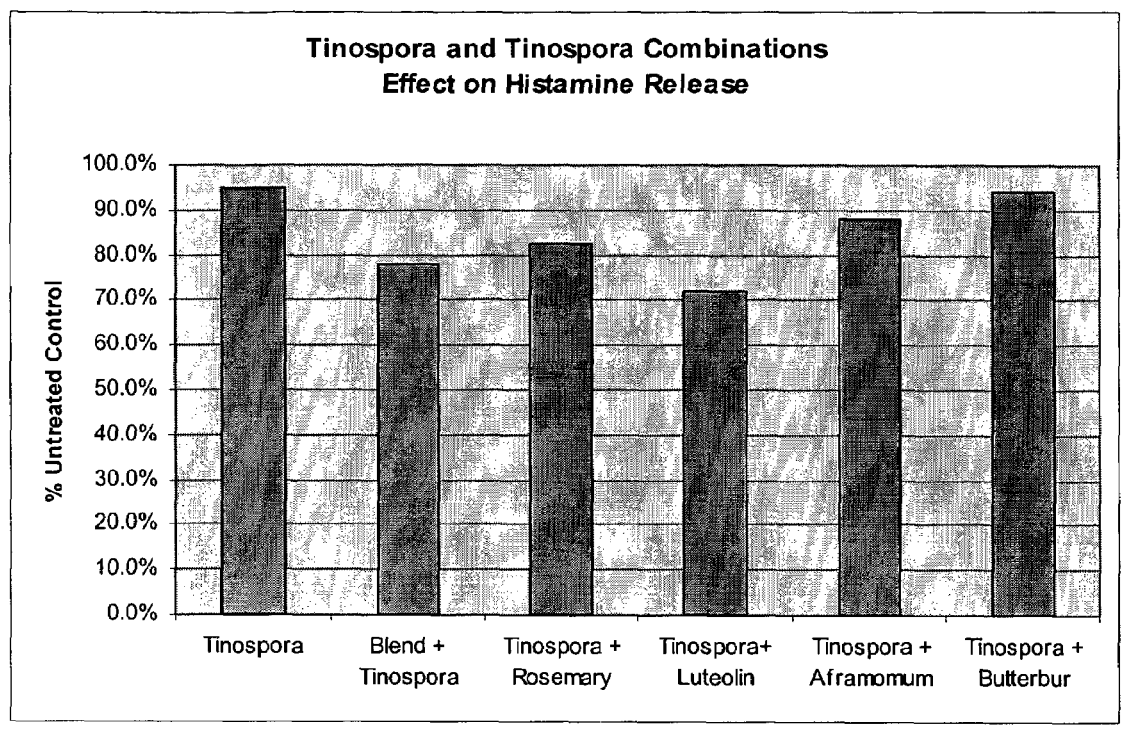

Another example of unexpected synergy is shown in FIG. 12 via the combination of tinospora with luteolin. There, the tinospora and luteolin combination inhibits histamine release to about 72%, whereas individually tinospora inhibited histamine release to about 95%, and luteolin to about 88%.

Figure 13:
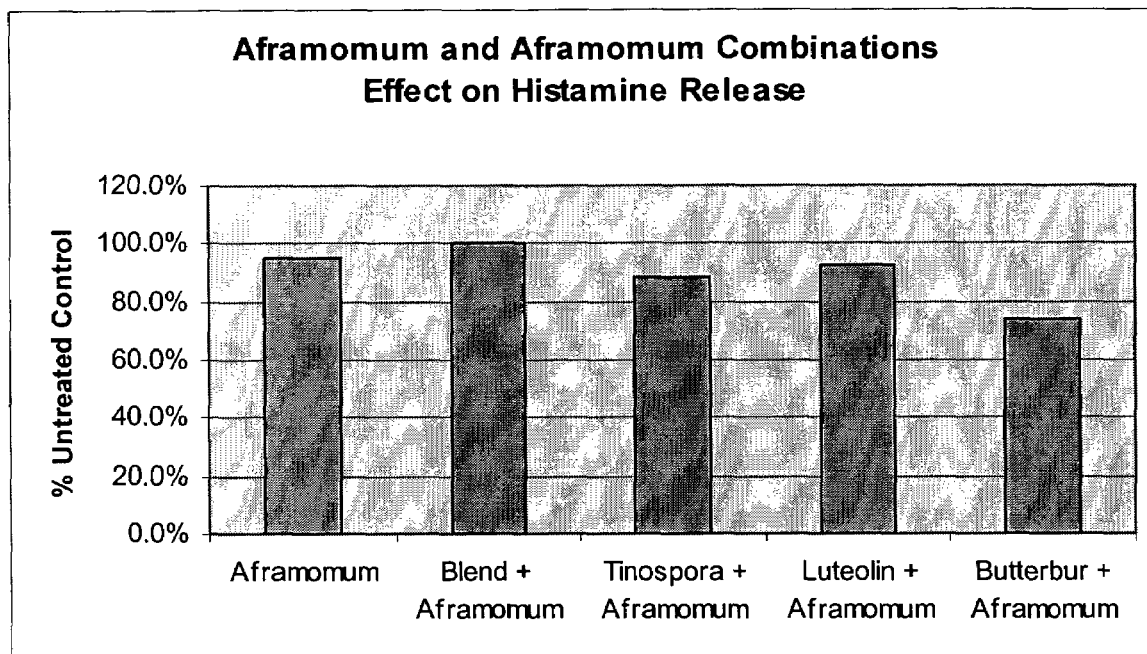

Yet another example of unexpected synergy is shown in FIG. 13 via the combination of the aframomum with butterbur. There, the combination inhibits histamine release to about 74%, whereas individually aframomum inhibits histamine release to about 73% and butterbur to about 75%.

C. Combined IgE and Allergy Mediator Testing and Results

For certain ingredients and combination of ingredients of the composition, both IgE down regulation and allergy mediator release were assessed contemporaneously. In an exemplary in-vitro model, both IgE down regulation and allergy mediator release were assessed following the methodologies presented in Examples 1 and 7, respectively. The following examples identify the compositions tested, and present the results of the testing.

EXAMPLE 9

Multiple ingredients and combinations of ingredients of the composition presented in Table VIII were tested to determine the effectiveness of each in both down regulating IgE and inhibiting histamine release. As used herein, the combination of luteolin (optionally from Perilla seed), Cinnamon and Acerola is referred to as the Formula. The concentration of each ingredient or combination of ingredients is noted in Table VIII. The concentration of each individual ingredient in the Formula was equal. For example, the Formula IgE-R (IgE receptor expression) concentration was 100 μg/ml. Thus, the concentration of luteolin from Perilla seed was 33.3 μg/ml, from Cinnamon was 33.3 μg/ml, and from Acerola was 33.3 μg/ml.

TABLE VIII

Effect of Ingredients on IgE Receptor Expression (IgE-R); IgE Secretion (IgE) and Histamine Release (Histamine)

| Ingredient | Ingredient Conc. | Percent Control |
|---|---|---|
| Luteolin from Perilla seed IgE-R | 100 μg/ml | 90.1% |
| Cinnamon IgE-R | 100 μg/ml | 119.9% |
| Acerola IgE-R | 100 μg/ml | 105.3% |
| Formula IgE-R | 100 μg/ml | 89.0% |
| Luteolin from Perilla seed IgE | 100 μg/ml | 95.5% |
| Cinnamon IgE | 100 μg/ml | 100.2% |
| Acerola IgE | 100 μg/ml | 77.9% |
| Formula IgE | | 76.0% |
| Luteolin from Perilla seed Histamine Release | 1 μg/ml | 99.9% |
| Cinnamon Histamine Release | 1 μg/ml | 77.5% |
| Acerola Histamine Release | 1 μg/ml | 58.6% |
| Formula Histamine Release | 1 μg/ml | 56.1% |

Figure 14:
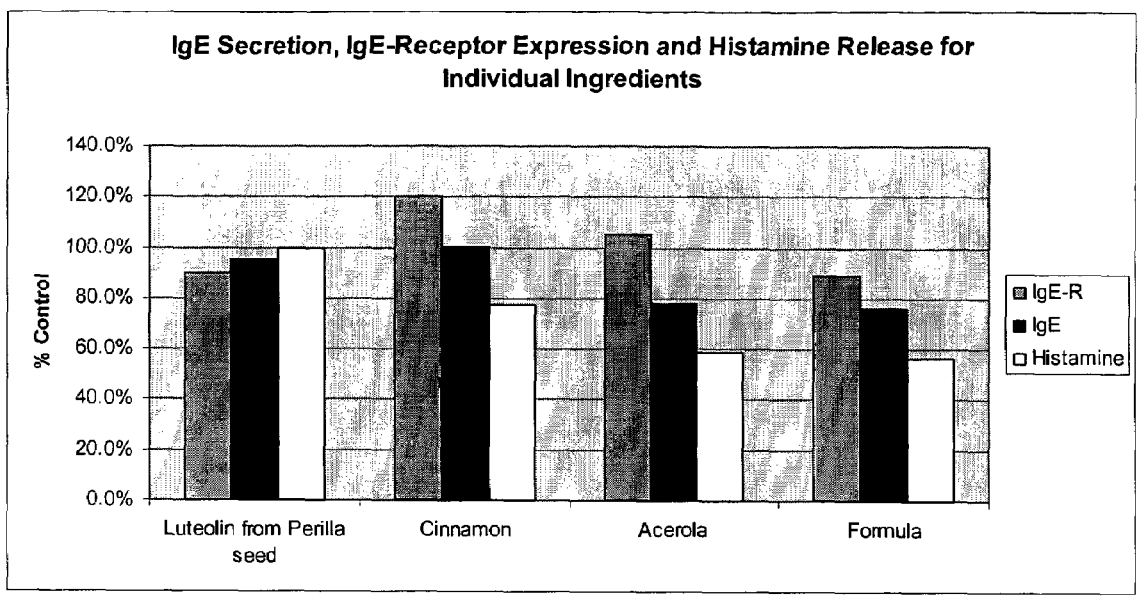
FIG. 14 is a graph illustrating the effect of multiple ingredient compositions on IgE secretion, IgE-Receptor expression and histamine release.

The data from Table VIII is illustrated in FIG. 14 to graphically demonstrate the effects of the different ingredients on IgE receptor expression, IgE secretion and histamine release. As shown in Table VIII and FIG. 14, most of the individual ingredients exhibited a positive effect on IgE receptor expression, IgE secretion and histamine release mediator release. However, surprising and unexpected synergy was observed when the ingredients were combined in the Formula. Specifically, the Formula inhibits histamine release as compared to a control (untreated with ingredients) to about 58%, whereas individually Luteolin inhibits histamine release to about 100%, Cinnamon to about 77% and Acerola to about 58%.

Further unexpected synergy is exhibited with respect to IgE down regulation. For example, the Formula down regulated IgE receptor expression to about 89%, whereas individually Luteolin inhibits IgE receptor expression to about 90%, Cinnamon to about 119% and Acerola to about 105%. As a further example, the Blend down regulated IgE secretion to about 76%, whereas individually Luteolin inhibits IgE secretion to about 95%, Cinnamon to about 100% and Acerola to about 78%.

The Formula may be combined with at least one of at least one of Picao preto, Tinospora, Rosmarinic acid, and Aframomum to elicit similar effects on IgE receptor expression, IgE secretion and mediator release.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A composition comprising approximately equal amounts of Cinnamon, Acerola cherry, and Picao preto, wherein the Cinnamon is in an amount by weight of about 5-33%, the Acerola cherry is in an amount by weight percent of about 5-33% and the Picao preto is in an amount by weight percent of about 5-33%, and wherein the composition is effective to inhibit an allergic response by at least one of down-regulating IgE expression, inhibiting IgE secretion and inhibiting an allergy mediator.

2. The composition of claim 1 further comprising at least one of a Luteolin ingredient, an Aframomum ingredient, a Rosmarinic acid ingredient and a Tinospora ingredient.

3. The composition of claim 2 comprising the Luteolin ingredient.

4. The composition of claim 1 wherein the luteolin is derived from Perilla leaf.

5. The composition of claim 1 wherein the Cinnamon, Acerola cherry and Picao preto are present in an effective amount to inhibit the allergy mediator, wherein the allergy mediator is at least one of prostaglandin D2, Leukotriene C4 and histamine.

6. The composition of claim 5 wherein the allergy mediator is prostaglandin $D_2$.

7. The composition of claim 5 wherein the allergy mediator is Leukotriene $C_4$.

8. The composition of claim 5 wherein the allergy mediator is histamine.

* * * * *